(12) United States Patent
Sherris

(10) Patent No.: US 9,381,187 B2
(45) Date of Patent: Jul. 5, 2016

(54) RADIATION COUNTERMEASURE AGENTS

(75) Inventor: David I. Sherris, Jamaica Plain, MA (US)

(73) Assignee: PALOMA PHARMACEUTICALS, INC., Charlottesville, VA (US)

(*) Notice: Subject to any disclaimer, the term of this patent is extended or adjusted under 35 U.S.C. 154(b) by 0 days.

(21) Appl. No.: 13/985,866

(22) PCT Filed: Feb. 16, 2012

(86) PCT No.: PCT/US2012/025475
§ 371 (c)(1),
(2), (4) Date: Nov. 12, 2013

(87) PCT Pub. No.: WO2012/112791
PCT Pub. Date: Aug. 23, 2012

(65) Prior Publication Data
US 2014/0100270 A1    Apr. 10, 2014

Related U.S. Application Data

(60) Provisional application No. 61/443,485, filed on Feb. 16, 2011.

(51) Int. Cl.
| A61K 31/35 | (2006.01) |
| A61K 31/366 | (2006.01) |
| A61K 31/37 | (2006.01) |
| A61K 31/4433 | (2006.01) |
| A61K 31/47 | (2006.01) |
| A61K 31/517 | (2006.01) |
| A61K 45/06 | (2006.01) |

(52) U.S. Cl.
CPC .............. *A61K 31/366* (2013.01); *A61K 31/37* (2013.01); *A61K 31/4433* (2013.01); *A61K 31/47* (2013.01); *A61K 31/517* (2013.01); *A61K 45/06* (2013.01)

(58) Field of Classification Search
CPC . A61K 31/366; A61K 31/37; A61K 31/4433; A61K 31/47; A61K 31/517; A61K 45/06
USPC ........................................................ 514/455
See application file for complete search history.

(56) References Cited

U.S. PATENT DOCUMENTS

| 4,248,861 A | 2/1981 | Schutt |
| 4,299,826 A | 11/1981 | Luedders |
| 4,363,812 A | 12/1982 | Kuriyama et al. |
| 5,851,785 A | 12/1998 | Aoyama et al. |
| 5,853,742 A | 12/1998 | Bartolone et al. |
| 6,172,241 B1 * | 1/2001 | Edwards et al. .............. 549/280 |
| 6,274,635 B1 | 8/2001 | Travis |
| 6,313,113 B1 | 11/2001 | Lohray et al. |
| 6,399,082 B1 | 6/2002 | Ganemo |
| 6,541,510 B2 | 4/2003 | Travis |
| 6,566,395 B1 | 5/2003 | Moran |
| 6,566,560 B2 | 5/2003 | Travis |
| 6,599,921 B2 | 7/2003 | Schmidt et al. |
| 6,632,835 B2 | 10/2003 | Schmidt et al. |
| 6,849,757 B2 | 2/2005 | Kawai et al. |
| 6,908,917 B2 | 6/2005 | Ortwine |
| 7,052,684 B2 | 5/2006 | Ferguson |
| 7,169,942 B2 | 1/2007 | Moore, II et al. |
| 7,220,413 B2 | 5/2007 | Ferguson |
| 7,326,447 B2 | 2/2008 | Taugerbeck et al. |
| 7,378,421 B2 | 5/2008 | Mujica-Fernaud et al. |
| 7,649,013 B2 * | 1/2010 | Li et al. .......................... 514/455 |
| 8,475,776 B2 * | 7/2013 | Sherris ............................ 424/60 |
| 2002/0115711 A1 | 8/2002 | Schmidt et al. |
| 2002/0119914 A1 | 8/2002 | Zhu et al. |
| 2003/0232101 A1 | 12/2003 | Travis |
| 2004/0138315 A1 | 7/2004 | Travis |
| 2004/0162281 A1 | 8/2004 | Babu et al. |
| 2004/0198750 A1 | 10/2004 | Green et al. |
| 2004/0242593 A1 | 12/2004 | Moore, II et al. |
| 2005/0245490 A1 | 11/2005 | Pinney et al. |
| 2006/0257337 A1 | 11/2006 | Sherris |
| 2007/0032469 A1 | 2/2007 | Isaac et al. |
| 2007/0179135 A1 | 8/2007 | Travis |
| 2007/0197567 A1 | 8/2007 | Sherris |
| 2008/0108647 A1 | 5/2008 | Travis |
| 2008/0159980 A1 | 7/2008 | Xu et al. |
| 2009/0203725 A1 | 8/2009 | Van Oeveren et al. |
| 2010/0183749 A1 * | 7/2010 | Brey .............................. 424/715 |
| 2010/0331400 A1 | 12/2010 | Ho et al. |
| 2011/0021618 A1 | 1/2011 | Sherris |
| 2011/0268679 A1 | 11/2011 | Sherris |
| 2012/0122917 A1 | 5/2012 | Travis |

(Continued)

FOREIGN PATENT DOCUMENTS

| AU | 7612874 | 6/1976 |
| DE | 24 59 076 | 7/1975 |

(Continued)

OTHER PUBLICATIONS

Diaz et al., "The novel Akt inhibitor Palomid 529 (P529) enhances the effect of radiotherapy in prostate cancer", 2009, British Journal of Cancer, vol. 2009, No. 6, pp. 932-940.*

International Search Report for International Application No. PCT/US2012/025475 mailed May 25, 2012, 3 pages.

Johansen, J. et al., "Relationship Between the In Vitro Radiosensitivity of Skin Fibroblasts and the Expression of the Subcutaneous Fibrosis, Telangiectasia, and Skin Erythema After Radiotherapy," Radiotherapy and Oncology, 1996, 40, 101-109.

Niemierko, A. et al., "Modeling of Normal Tissue Response to Radiation: The Critical Volume Model," International Journal of Radiation Oncology Biology Physics, 1992, 25, 135-145.

Weiss, J. et al., "Protection Against Ionizing Radiation by Antioxidant Nutrients and Phytochemicals," Toxicology, 2003, 189, 1-20.

(Continued)

*Primary Examiner* — My-Chau T Tran
(74) *Attorney, Agent, or Firm* — Hoxie & Associates LLC

(57) ABSTRACT

Methods and compositions for reducing radiation damage in a subject with analog or derivative of benzo[c]chromen-6-one.

29 Claims, 4 Drawing Sheets

(56) References Cited

U.S. PATENT DOCUMENTS

| | | |
|---|---|---|
| 2013/0310576 A1 | 11/2013 | Kudou et al. |
| 2013/0336935 A1 | 12/2013 | Niedernhofer et al. |
| 2014/0100270 A1 | 4/2014 | Sherris |
| 2014/0105920 A1 | 4/2014 | Sherris |
| 2014/0221471 A1 | 8/2014 | Sherris |

FOREIGN PATENT DOCUMENTS

| | | |
|---|---|---|
| EP | 0 645 382 A1 | 3/1995 |
| ES | 484 472 | 5/1980 |
| WO | WO 93/15219 A1 | 8/1993 |
| WO | WO 00/56303 A2 | 9/2000 |
| WO | WO 01/03681 A2 | 1/2001 |
| WO | WO 01/46110 A2 | 6/2001 |
| WO | WO 02/086078 A2 | 10/2002 |
| WO | WO 02/094984 A2 | 11/2002 |
| WO | WO 03/105842 A1 | 12/2003 |
| WO | WO 2004/073612 A2 | 9/2004 |
| WO | WO 2005/117876 A1 | 12/2005 |
| WO | WO 2007/101247 A2 | 9/2007 |
| WO | WO 2007/133249 A2 | 11/2007 |
| WO | WO 2009/120799 A2 | 10/2009 |
| WO | WO 2010/129622 A1 | 11/2010 |
| WO | WO 2011/144578 A1 | 11/2011 |
| WO | WO 2012/175973 A1 | 12/2012 |
| WO | WO 2015/154047 A1 | 10/2015 |

OTHER PUBLICATIONS

Written Opinion of the International Searching Authority for International Application No. PCT/US2012/025475 mailed May 25, 2012, 4 pages.
U.S. Appl. No. 14/789,935, filed Jun. 1, 2015, Sherris et al.
Abstract for ES 484 472 retrieved from http://translationportal.epo.org/emtp/translate/?ACTION=abstract-retrieval&COUNTRY=ES&ENGINE=google&FORMAT=docdb&KIND=A1&LOCALE=en_EP&NUMBER=484472&OPS=ops.epo.org/3.1&SRCLANG=es&TRGLANG=en on Mar. 25, 2015, 2 pages.
Adams, R. et al., "Structure of Cannabinol. 1. Preparation of an Isomer, 3-hydroxy-1-amyl-6,6,9-trimethyl-6-dibenzopyran," Journal of the American Chemical Society, 1940, 62, 2197-2200, XP002563538, Chemical Abstracts only, 1 page.
Aoyama, N. et al., "Coumarin Derivatives for Quantitative Determination of Peroxidation-Active Substances by Chemiluminescence Analysis," Chemical Abstracts, 1993, XP002563539, Chemical Abstracts only, 1 page.
Benjamin, D. et al., "Rapamycin Passes the Torch: A New Generation of mTOR Inhibitors," Nature Reviews Drug Discovery, 2011, 10 (11), 868-880.
Bisht, M. et al., "Angiogenesis: Future of Pharmacological Modulation," Indian Journal of Pharmacology, 2010, 42 (1), 2-8.
Byun, J. "Quantitative Analysis and Modeling of Confocal Retinal Images," Dissertation, University of California Santa Barbara, copyright 2007, 238 pages.
Cao, K. et al., "Rapamycin Reverses Cellular Phenotypes and Enhances Mutant Protein Clearance in Hutchinson-Gilford Progeria Syndrome Cells," Science Translational Medicine, 2011, 3 (89), 89ra58, 13 pages.
Carl, P. et al., "Protease-activated 'Prodrugs' for Cancer Chemotherapy" Proceedings of the National Academy of Sciences, 1980, 77 (4), 2224-2228.
Carmeliet, P. et al., "Angiogenesis in Cancer and Other Diseases," Nature, 2000, 407, 249-257.
Carmeliet, P., "Angiogenesis in Life, Disease and Medicine," Nature, 2005, 438, 932-936.
CAS Registry Entry 2555-22-8, entered STN Nov. 16, 1984, 1 page.
CAS Registry Entry 20043-65-6, entered STN Nov. 16, 1984, 1 page.
CAS Registry Entry 262591-03-7, entered STN Apr. 21, 2000, 1 page.
CAS Registry Entry 304880-11-3, entered STN Nov. 29, 2000, 1 page.
CAS Registry Entry 307524-30-7, entered STN Dec. 8, 2000, 1 page.
CAS Registry Entry 314744-92-8, entered STN Jan. 18, 2001, 1 page.
CAS Registry Entry 332104-52-6, entered STN Apr. 24, 2001, 1 page.
CAS Registry Entry 380322-78-1, entered STN Jan. 3, 2002, 1 page.
CAS Registry Entry 405916-57-6, entered STN Apr. 18, 2002, 1 page.
CAS Registry Entry 406476-00-4, entered STN Apr. 22, 2002, 1 page.
CAS Registry Entry 883805-65-0, entered STN May 11, 2006, 1 page.
CAS Registry Entry 914913-88-5, entered STN Dec. 6, 2006, 1 page.
CAS Registry Entry 914914-00-4, entered STN Dec. 6, 2006, 1 page.
CAS Registry Entry 914914-21-9, entered STN Dec. 6, 2006, 1 page.
CAS Registry Entry 914914-25-3, entered STN Dec. 6, 2006, 1 page.
CAS Registry Entry 914914-34-4, entered STN Dec. 6, 2006, 1 page.
CAS Registry Entry 914914-36-6, entered STN Dec. 6, 2006, 1 page.
CAS Registry Entry 1026201-80-8, Entered STN Jun. 8, 2008, 1 page.
CAS Registry Entry 1026498-34-9, Entered STN Jun. 8, 2008, 1 page.
Chapin, E. et al., "Müller Cell Proliferation and Glial Scar Formation Is Reduced Following Experimental Retinal Detachment Using Palomid 529, an Inhibitor of the Akt/mTOR Pathway," retrieved from http://abstracts.iovs.org//cgi/content/abstract/49/5/5183 on Mar. 25, 2015, 2 pages (face of abstract states Investigative Ophthalmology & Visual Science, copyright 2008, 49: E-Abstract 5183).
Children's Hospital, Atopic Dermatitis—Treatment, Care, & FAQ, retrieved from http://childrenshospital.org/az/Site609/mainpageS609P4.html, retrieved Jul. 6, 2012, 8 pages.
Chugh, P. et al., "Akt Inhibitors as an HIV-1 Infected Macrophage-Specific Anti-Viral Therapy," Retrovirology, 2008, 5:11, doi:10.1186/1742-4690-5-11, 13 pages.
Costabel, U., "Emerging Potential Treatments: New Hope for Idiopathic Pulmonary Fibrosis Patients?," European Respiratory Review, 2011, 20 (121), 201-207.
Coward, W. et al., "The Pathogenesis of Idiopathic Pulmonary Fibrosis," Therapeutic Advances in Respiratory Disease, 2010, 4 (6), 367-388.
Derwent Abstract for IN 200400392 which indicates IN 200400392 published Feb. 24, 2006, abstract retrieved Jul. 9, 2007, 3 pages.
Devlin, J. et al., "Synthesis and Structure Activity Relationships of 5H, 11H[2]Benzopyrano[4,3g][1]benzopyran-9-carboxylic Acids," Journal of Medicinal Chemistry, 1977, 20 (2), 205-209.
Diehl, N. et al., "Make Yourself at Home: Viral Hijacking of the PI3K/Akt Signaling Pathway," Viruses, 2013, 5, 3192-3212.
Dienstmann, R. et al., "Picking the Point of Inhibition: A Comparative Review of PI3K/AKT/mTOR Pathway Inhibitors," Molecular Cancer Therapeutics, 2014, 13, 1021-1031.
Dunn, E. et al., "HijAkt: The PI3K/Akt Pathway in Virus Replication and Pathogenesis," Progress in Molecular Biology and Translational Science, 2012, 106, 223-250.
Eibl, K. et al., "The Effect of Alkylphosphocholines on Intraretinal Proliferation Initiated by Experimental Retinal Detachment," Investigative Ophthalmology and Visual Science, 2007, 48 (3), 1305-1311.
Extended European Search Report issued by the European Patent Office in European Patent Application No. 12171867.0, dated Dec. 14, 2012, 13 pages.
Farina, V. et al., "The Stille Reaction," Organic Reactions, 1997, 50, XP002563537, Chemical Abstracts only, 1 page.
Garazd, Y. et al., "Modified Coumarins. 6. Synthesis of Substituted 5,6-Benzopsoralens," Chemistry of Natural Compounds, 2002, 38 (5), 424-433.
Garazd, Y. et al., "Modified Couramins. 6. Synthesis of Substituted 5,6-Benzopsoralens," Chemistry of Natural Compounds, 2002, 38 (5), 424-433, XP002563541, Chemical Abstracts only, 2 pages.
Gaur, P. et al., "Influenza Virus and Cell Signaling Pathways," Medical Science Monitor, 2011, 17 (6), RA148-154.
Gharbi, S. et al., "Exploring the Specificity of the PI3K Family Inhibitor LY294002," Biochemical Journal, 2007, 404, 15-21.

(56) References Cited

OTHER PUBLICATIONS

Gnerre, C. et al., "Inhibition of Monoamine Oxidases by Functionalized Coumarin Derivatives: Biological Activities, QSARs, and 3D-QSARs," Journal of Medicinal Chemistry, 2000, 43, 4747-4758.
Gravina, G. et al., "The TORC1/TORC2 Inhibitor, Palomid 529, Reduces Tumor Growth and Sensitizes to Docetaxel and Cisplatin in Aggressive and Hormone-Refractory Prostate Cancer Cells," Endocrine-Related Cancer, 2011, 18, 385-400.
Gupta, R. et al., "Protection of Mouse Chromosomes Against Whole-Body Gamma Irradiation by SH-Compounds," The British Journal of Radiology, 1986, 59, 625-627.
Hörig, H. et al., "From Bench to Clinic and Back: Perspective on the 1st IQPC Translation Research Conference," Journal of Translational Medicine, 2004, 2 (44), doi:10.1186/1479-5876-2-44, 8 pages.
Horowitz, J. et al., "Mechanisms of Signal Transduction: Activation of the Pro-Survival Phosphatidylinositol 3-Kinase/AKT Pathway by Transforming Growth Factor-β1 in Mesenchymal Cells Is Mediated by p38 MAPK-Dependent Induction of an Autocrine Growth Factor," The Journal of Biological Chemistry, 2004, 279 (2), 1359-1367.
International Preliminary Report on Patentability for International Application No. PCT/US2006/040242, Date of issuance of the report Jan. 20, 2009, 4 pages.
International Preliminary Report on Patentability for International Application No. PCT/US2007/062971, Date of issuance of the report Sep. 2, 2008, 6 pages.
International Preliminary Report on Patentability for International Application No. PCT/US2009/038285, Date of issuance of the report Sep. 28, 2010, 4 pages.
International Search Report for International Application No. PCT/US2006/040242 mailed Dec. 9, 2008, 2 pages.
International Search Report for International Application No. PCT/US2007/062971, mailed Oct. 1, 2007, 3 pages.
International Search Report for International Application No. PCT/US2015/024371, mailed Jun. 26, 2015, 3 pages.
Ishiguro, I. et al., "Isolation and Identification of the 2-Methyl-1,2,3,4-tetrahydro-4-quinazolone as a New Metabolite in the Urine of Anthranilic Acid Injected Rats," Journal of the Pharmaceutical Society of Japan, 1974, 94 (10), 1232-1239.
Kenner, G. et al., "Oxidative Cyclization of 2-Biphenylcarboxylic Acid," Tetrahedron, 1957, 1, 259-268, XP002563536, Chemical Abstracts only, 1 page.
Kim, S. et al., "Caveolin-1 Increases Basal and TGF-β1-Induced Expression of Type I Procollagen Through PI-3 Kinase/Akt/mTOR Pathway in Human Dermal Fibroblasts," Cellular Signaling, 2008, 20, 1313-1319.
Kurita, M. et al., "Induction of Keratinocyte Apoptosis by Photosensitizing Chemicals Plus UVA," Journal of Dermatological Science, 2007, 45, 105-112.
Lamouille, S. et al., "Emergence of the Phosphoinositide 3-Kinase-Akt-Mammalian Target of Rapamycin Axis in Transforming Growth Factor-β-Induced Epithelial-Mesenchymal Transition," Cell Tissues Organs, 2011, 193, 8-22.
Larrosa, M. et al., "Urolithins, Ellagic Acid-Derived Metabolites Produced by Human Colonic Microflora, Exhibit Estrogenic and Antiestrogenic Activities," Journal of Agricultural and Food Chemistry, 2006, 54, 1611-1620.
Lewis, G. et al., "Müller Cell Reactivity and Photoreceptor Cell Death Are Reduced after Experimental Retinal Detachment Using an Inhibitor of the Akt/mTOR Pathway," Investigative Ophthalmology and Visual Science, 2009, 50 (9), 4429-4435.
Li, X. et al., "Mammalian Target of Rapamycin Inhibition in Macrophages of Asymptomatic HIV+Persons Reverses the Decrease in TLR-4-Mediated TNF-α Release through Prolongation of MAPK Pathway Activation," The Journal of Immunology, 2011, 187, 6052-6058.
Lin, F. et al., "Dual mTORC1 and mTORC2 Inhibitor Palomid 529 Penetrates the Blood-Brain Barrier without Restriction by ABCB1 and ABCG2," International Journal of Cancer, 2013, 133 (5), 1222-1233.
Liu, S. et al., "Facilitation of Retinal Function Recovery by Coumarin Derivatives," Journal of Ocular Pharmacology and Therapeutics, 1997, 13 (1), 69-79.
Lopez-Gonzalez, J. et al., "Apoptosis and Cell Cycle Disturbances Induced by Coumarin and 7-Hydroxycoumarin on Human Lung Carcinoma Cell Lines," Lung Cancer, 2004, 43, 275-283.
Mao, Z. et al., "Natural Dibenzo-α-Pyrones and Their Bioactivities," Molecules, 2014, 19, 5088-5108.
Mendelsohn, A. et al., "Rapamycin as an Antiaging Therapeutic?: Targeting Mammalian Target of Rapamycin to Treat Hutchinson-Gilford Progeria and Neurodegenrative Diseases," Rejuvenation Research, 2011, 14 (4), 437-441.
Nicoletti, F. et al., "mTor as a Multifunctional Therapeutic Target in HIV Infection," Drug Discovery Today, 2011, 16 (15/16), 715-721.
Novaroli, L. et al., "Human Recombinant Monoamine Oxidase B as Reliable and Efficient Enzyme Source for Inhibitor Screening," Bioorganic and Medicinal Chemistry, 2005, 13, 6212-6217.
Oklu, R. et al., "Angiogenesis and Current Antiangiogenic Strategies for the Treatment of Cancer," Journal of Vascular and Interventional Radiology, 2010, 21, 1791-1805.
"Paloma Pharmaceuticals to Present at the Association for Research in Vision and Ophthalmology," dated 2008, 1 page, retrieved from http://www.palomapharma.com/dfiles/news/8%20February%202008%20news%20entry.pdf (website last accessed Jan. 17, 2014).
Planz, O., "Development of Cellular Signaling Pathway Inhibitors as New Antivirals Against Influenza," Antiviral Research, 2013, 98, 457-468.
PubChem, CID 11998812, Create Date Feb. 5, 2007, available at http://pubchem.ncbi.nlm.nih.gov/summary/summary.cgi?cid=11998812, retrieved Sep. 13, 2013, 3 pages.
PubChem, CID 11998813, Create Date Feb. 5, 2007, available at http://pubchem.ncbi.nlm.nih.gov/summary/summary.cgi?cid=11998813, retrieved Sep. 13, 2013, 3 pages.
Registry Entries of 406476-00-4, 405916-57-6, 380322-78-1, 314744-92-8, and 304880-11-3.
Rice, C. et al., "From Antiangiogenesis to Hypoxia: Current Research and Future Directions," Cancer Management and Research, 2011, 3, 9-16.
Rigaudy, J. et al., "Dehydration of Meso-dihydroanthracene Alcohols. 9,10-Dihydro-9-anthryl Tertiary Carbinols. A Case of Elimination (of water) According to Hofmann's Rule," Comptes Rendus, 1957, 245, 86-88, XP002563540, Chemical Abstracts only, 1 page.
Rosenbloom, J. et al., "Strategies for Anti-Fibrotic Therapies," Biochimica et Biophysica Acta, 2013, 1832, 1088-1103.
Sabatini, D. et al., "RAFT1: A Mammalian Protein that Binds to FKBP12 in a Rapamycin-Dependent Fashion and is Homologous to Yeast TORs," Cell, 1994, 78, 35-43.
Sakai, N. et al., "Fibrosis of Two: Epithelial Cell-Fibroblast Interactions in Pulmonary Fibrosis," Biochimica et Biophysica Acta, 2013, 1832, 911-921.
Sapuntsova, S. et al., "Proliferative Processes in the Epidermis of Patients with Atopic Dermatitis Treated with Thymodepressin," Bulletin of Experimental Biology and Medicine, 2002, 133 (5), 488-490.
Savage, J., "Classification and Relationships of Induced Chromosomal Structural Changes," Journal of Medical Genetics, 1975, 12, 103-122.
Schäfer S. et al., "Failure is an Option: Learning from Unsuccessful Proof-of-concept Trials," Drug Discovery Today, 2008, 13 (21/22), 913-916.
Schechter, R. et al., "CNS Sterile Injury: Just Another Wound Healing?," Trends in Molecular Medicine, 2013, 19 (3), 135-143.
Schmidt, J. et al., "Synthesis and Evaluation of a Novel Nonsteroidal-Specific Endothelial Cell Proliferation Inhibitor," Journal of Medicinal Chemistry, 2003, 46, 1289-1292.
Shi-Wen, X. et al., "Endothelin-1 Promotes Myofibroblast Induction through the ETA Receptor via a rac/Phosphoinositide 3-Kinase/Akt-dependent Pathway and Is Essential for the Enhanced Contractile Phenotype of Fibrotic Fibroblasts," Molecular Biology of the Cell, 2004, 15, 2707-2719.

(56) References Cited

OTHER PUBLICATIONS

Sureshbabu, A. et al., "Relative Roles of TGF-β and IGFBP-5 in Idiopathic Pulmonary Fibrosis," Pulmonary Medicine, Article ID 517687, 6 pages, doi:10.1155/2011/517687.
Syed, F. et al., "Keloid Disease Can Be Inhibited by Antagonizing Excessive mTOR Signaling with a Novel Dual TORC1/2 Inhibitor," The American Journal of Pathology, 2012, 181 (5), 1642-1658.
The Acne Resource Center Online, Your Online Guide to Skincare, http://www.acne-resource.org/understanding-acne/understanding-index.html, retrieved Jul. 6, 2012, 2 pages.
Turnell, a. et al., "DNA Viruses and the Cellular DNA-Damage Response," Journal of General Virology, 2012, 93, 2076-2097.
Umamoto, H. et al., "Fluorescent Whitening Agents for Synthetic Fiber," Kogyo Kagaku Zasshi, 1971, 74 (10), 2123-2126, Chemical Abstracts only, XP-002563541, 2 pages.
Vanhaesebroeck, B. et al., "PI3K Signalling: The Path to Discovery and Understanding," Nature Reviews, 2012, 13, 195-203.
Vilar, S. et al., "Design, Synthesis, and Vasorelaxant and Platelet Antiaggregatory Activities of Coumarin-Resveratrol Hybrids," Bioorganic and Medicinal Chemistry Letters, 2006, 16, 257-261.
Vilar, E. et al., "Pushing the Envelope in the mTOR Pathway: The Second Generation of Inhibitors," Molecular Cancer Therapeutics, 2011, 10, 395-403.
Wolff, M., Burger's Medicinal Chemistry and Drug Discovery, 1995, 5th edition, vol. I: Principles and Practice, pp. 975-977.
Written Opinion of the International Searching Authority mailed Dec. 9, 2008, for International Application No. PCT/US2006/040242, 3 pages.
Written Opinion of the International Searching Authority mailed Jun. 26, 2015, for International Application No. PCT/US2015/024371, 4 pages.
Wynn, T., "Cellular and Molecular Mechanisms of Fibrosis," Journal of Pathology, 2008, 214, 199-210.
Xie, T. et al., "Regulation of Keratinocyte Proliferation in Rats with Deep, Partial-Thickness Scald: Modulation of Cyclin D1-Cyclin-Dependent Kinase 4 and Histone H1 Kinase Activity of M-Phase Promoting Factor," Journal of Surgical Research, 2008, 147 (1), 9-14.
Xue, Q. et al., "Palomid 529, A Novel Small-Molecule Drug, Is a TORC1/TORC2 Inhibitor that Reduces Tumor Growth, Tumor Angiogenesis, and Vascular Permeability," Cancer Research, 2008, 68, 9551-9557.
Yano, K. et al., "Targeted Overexpression of the Angiogenesis Inhibitor Thrombospondin-1 in the Epidermis of Transgenic Mice Prevents Ultraviolet-B-Induced Angiogenesis and Cutaneous Photodamage," Journal of Investigative Dermatology, 2002, 118 (5), 800-805.
Yoo, H. et al., "Biodegradable Nonoparticles Containing Doxorubicin-PLGA Conjugate for Sustained Release," Pharmaceutical Research, 1999, 16 (7), 1114-1118.
Yuan, J. et al., "PF-04691502, A Potent and Selective Oral Inhibitor of PI3K and mTOR Kinases with Antitumor Activity," Molecular Cancer Therapeutics, 2011, 10 (11), 2189-2199.
Zhang, Y. et al., "Study on the Synthesis and Spectra Characteristics of Coumarins," Ranliao Yu Ranse Bianjibu, 2003, 40 (2), 68-70, XP002563541, Chemical Abstracts only, 2 pages.
Requirement for Restriction Election mailed Nov. 13, 2009, in U.S. Appl. No. 11/412,618, 11 pages.
Non-Final Office Action dated Mar. 22, 2010, in U.S. Appl. No. 11/412,618, 14 pages.
Final Office Action dated Jul. 22, 2010, in U.S. Appl. No. 11/412,618, 13 pages.
Notice of Allowance and Interview Summary mailed Apr. 11, 2011, in U.S. Appl. No. 11/412,618, 10 pages.
Requirement for Restriction Election dated Mar. 11, 2010, in U.S. Appl. No. 11/680,292, 11 pages.
Non-Final Office Action dated May 11, 2010, in U.S. Appl. No. 11/680,292, 16 pages.
Final Office Action dated Oct. 14, 2010, in U.S. Appl. No. 11/680,292, 12 pages.
Notice of Allowance and Interview Summary mailed Sep. 14, 2012, in U.S. Appl. No. 11/680,292, 8 pages.
Notice of Allowance and Interview Summary mailed Feb. 20, 2013, in U.S. Appl. No. 11/680,292, 9 pages.
Non-Final Office Action mailed Feb. 21, 2013, in U.S. Appl. No. 12/934,010, 19 pages.
Final Office Action dated Aug. 8, 2013, in U.S. Appl. No. 12/934,010, 14 pages.
Notice of Allowance mailed Jan. 13, 2015, in U.S. Appl. No. 12/934,010, 10 pages.
Notice of Allowance mailed May 19, 2015, in U.S. Appl. No. 12/934,010, 8 pages.
Requirement for Restriction Election mailed May 23, 2012, in U.S. Appl. No. 13/180,149, 10 pages.
Non-Final Office Action mailed Jul. 23, 2012, in U.S. Appl. No. 13/180,149, 15 pages.
Final Office Action mailed Jan. 2, 2013, in U.S. Appl. No. 13/180,149, 8 pages.
Requirement for Restriction Election dated Jun. 4, 2014, in U.S. Appl. No. 13/901,011, 10 pages.
Non-Final Office Action dated Jan. 12, 2015, in U.S. Appl. No. 13/901,011, 12 pages.
Final Office Action dated Aug. 21, 2015, in U.S. Appl. No. 13/901,011, 11 pages.
Non-Final Office Action dated Aug. 15, 2014, in U.S. Appl. No. 14/171,214, 14 pages.
Notice of Allowance mailed Mar. 25, 2015, in U.S. Appl. No. 14/171,214, 6 pages.
Notice of Allowance mailed Jul. 27, 2015, in U.S. Appl. No. 14/171,214, 7 pages.
Notice of Allowance mailed Nov. 24, 2015, in U.S. Appl. No. 14/171,214, 7 pages.

\* cited by examiner

RADIATION COUNTERMEASURE AGENTS

CROSS REFERENCE TO RELATED APPLICATIONS

The present application is the National Stage Entry under 35 U.S.C. §371 of International Application No. PCT/US2012/025475 filed Feb. 16, 2012, which claims priority to U.S. Provisional Application No. 61/443,485, filed Feb. 16, 2011, the contents of each of which are incorporated by reference.

BACKGROUND

The development of safer and more effective radioprotectors is critical to protecting civilians from unintended radiation exposure in this currently heightened nuclear threat environment. Radioprotective agents are needed to protect people not only from acute, early arising (radiation syndrome) effects, but late arising (cancer) radiation pathologies as well. Development of a radioprotector that could both decrease acute radiation effects as well as prevent development of radiation-induced cancer would be of significant benefit to an exposed population and would be more than just an incremental improvement in radioprotection. Currently there are no safe and effective radioprotectors that have been approved by the U.S. Food and Drug Administration (FDA) for human use in a non-clinical setting, i.e., dirty bomb, nuclear accident. Several drugs are in different stages of evaluation, but so far none possesses all the requisite qualities to be an optimum radioprotector. Therefore, there is a significant gap in our knowledge and identification of effective and safe non-toxic radioprotectors. Development of new pre- and postexposure treatment products that will protect against and/or mitigate the effects of short- and long-term consequences of external radiation exposure and/or internal contamination with radionuclides is critical. With the significant improvements in clinical treatments of acute radiation injury, more attention needs to be paid to prevention of radiation-induced late effects like cancer and leukemia as well.

The several radioprotective agents that are currently approved for human use are for either clinical use or very selective and limited radiation exposure situations. The most well known of these agents is amifostine which is known for its radioprotective properties and its well-understood mechanism. Although amifostine is considered the "gold standard" of radioprotectors, it is toxic to animals and humans at radioprotective doses. Strategies to overcome the toxicity of amifostine have been minimally successful by chemically modifying the parent drug or combining with other low toxicity drugs. Several other radioprotectants with highly specific indications include potassium iodide or calcium/zinc diethylenetriaminepentaacetic acid (DTPA) but have limited usefulness as systemic radioprotectors in the event of nuclear exposure to military personnel. Immuno-modulators like the androstene steroids represent a newer approach to radioprotection. The compound 5-androstenediol (5-AED) has demonstrated significant radioprotective capability in vivo at non-toxic doses (8). Its usefulness, however, could be limited due to ineffective oral delivery and injection site inflammatory responses. Additional recent approaches have included the study of neutraceuticals, i.e., alpha tocopherol, genistein, and plant flavonoids. These approaches have shown promise but are limited by the necessity for high doses, poor oral delivery systems, and low dose reduction factors (DRF). While there are a number of cutting edge technologies like bioengineered "designer" growth factors, their feasibility for use in humans is untested and unknown. Furthermore, with the exception of amifostine, none of these approaches has shown any effectiveness against late arising radiation pathologies. Amifostine however, has not received approval for use as a radioprotector for civilian or military populations. Efforts to develop a radioprotector that can prevent long-term health effects of radiation exposure have been limited and represent a significant gap in the understanding of how to protect civilian and military personnel from health hazards of ionizing radiation.

It is well known that radiation exposure can lead to cancer development and in particular to development of leukemia. Risk estimates for radiation leukemogenesis and carcinogenesis are based on experience in humans. Quantitative data on cancer induction by radiation come from populations irradiated for medical purposes (diagnostic, radiotherapy) or inadvertently to nuclear weapons. While there is significant human and animal data regarding the induction of radiation-induced cancers, there is little data regarding the development of chemopreventive approaches to preventing these late-arising radiation sequelae. Amifostine which has is well known as a radioprotector of acute radiation effects, had shown some effectiveness at preventing radiation-late effects, i.e., cancer. In cellular and animals models it has demonstrated anti-mutagenic and anti-carcinogenic properties. While amifostine would appear to have a broad usefulness as both a radiation cytoprotective and chemopreventive agent, its use as a radioprotectant is limited by its significant toxicity. Therefore it is critical to continue the search to identify radioprotective agents that could protect against both acute and long-term radiation health effects.

BRIEF SUMMARY

The problems set forth above as well as further and other problems are solved by the present teachings. These solutions and other advantages are achieved by the various embodiments of the teachings described herein below.

In one embodiment, the method of these teachings for reducing radiation damage in a subject includes the steps of administering to the subject an effective amount of an agent, wherein the agent is an analog or derivative of benzo[c]chromen-6-one.

In a further aspect, the method of these teachings for reducing radiation damage in a subject by administering to the subject an effective amount of an agent, wherein the agent is administered after radiation exposure.

In a further aspect, the method of these teachings for reducing radiation damage in a subject by administering to the subject an effective amount of an agent, wherein the agent is administered before radiation exposure.

In one embodiment, the pharmaceutical composition of these teachings includes a therapeutically effective amount of at least one of the disclosed compounds and a pharmaceutically acceptable carrier.

In a further aspect, the method of these teachings for mitigating radiation toxicity in a subject includes the steps of administering to the subject at least one of the disclosed compounds or at least one of the disclosed pharmaceutical compositions in a dosage and amount effective to mitigate radiation toxicity in the subject.

The present invention also provides the following methods:

A method for reducing radiation damage, reducing potential damage by exposure to radiation, treating damage caused by exposure to radiation, and/or inhibiting formation of damage caused by radiation in a subject comprising administering to the subject an effective amount of an agent which is an analog or derivative of benzo[c]chromen-6-one.

The wherein the agent may be administered to the subject before the subject has been exposed to radiation, i.e., within 1 hour, 2 hours, 3 hours, 6 hours, 12 hours, 1 day, or 2 days after exposure. Alternatively, the agent may be administered to the subject before the subject has been exposed to radiation, i.e., 2 days, 1 day, 12 hours, 6 hours, 3 hours, 2 hours, 1 hour, 30 minutes, or 15 minutes prior to exposure.

The agent utilized in the present methods may be formula I, II, III or IV in free or pharmaceutically acceptable salt form, or may be selected from an agent provided in Table 1.

Methods of the present invention may be useful wherein the radiation is ionizing radiation, i.e., gamma radiation.

It is contemplated that the compositions and methods of this invention may be useful for a variety of mammals, including humans and non-human mammals such as non-human primates (e.g., monkeys, chimpanzees, etc.), companion animals (e.g., dogs, cats, rabbits, equine, etc.), farm animals (e.g., goats, sheep, swine, bovine, etc.), laboratory animals (e.g., mice, rats, etc.), and wild and zoo animals (e.g., wolves, bears, deer, etc.). Compositions and methods of the present invention may also be useful for other vertebrate, for example, a fish, bird, and reptile.

In certain embodiments, the subject is suffering from or will likely suffer from acute radiation syndrome or radiation sickness, suffering from cancer and undergoing radiation therapy and/or chemotherapy. Compositions and methods of the present invention may be useful if the subject is suffering from leucopenia, neutropenia, purpura, hemorrhage, diarrhea, vomiting, and/or hypotension.

Compositions and methods of the present invention may further include administration of a cytoprotective agent, or other compounds which inhibits the PI3K/Akt/mTOR pathway. In certain embodiments of the present invention, the an agent is administered every hour, 2 hours, 3 hours, 6 hours, or daily following exposure to radiation in order to achieve a blood plasma level of about 0.1 to about 1000 μM. A dose of the agent may be from about 0.1 to about 1000 mg/kg.

Compositions of the present invention may include pharmaceutical composition comprising an effective amount of a compound of formula I, formula II, formula III, and/or formula IV in combination with an effective amount of a cytoprotective agent in a pharmaceutically acceptable carrier, i.e., for use in reducing radiation damage, reducing potential damage by exposure to radiation, treating damage caused by exposure to radiation, and/or inhibiting formation of damage caused by radiation.

Also contemplated in the present invention is use of a compound of formula I, formula II, formula III, or formula IV in free or pharmaceutically acceptable salt form in manufacturing a medicament for reducing radiation damage, reducing potential damage by exposure to radiation, treating damage caused by exposure to radiation, and/or inhibiting formation of damage caused by radiation in a subject in need thereof.

For a better understanding of the present teachings, together with other and further objects thereof, reference is made to the accompanying drawings and detailed description and its scope will be pointed out in the appended claims.

DETAILED DESCRIPTION

Figure 1:
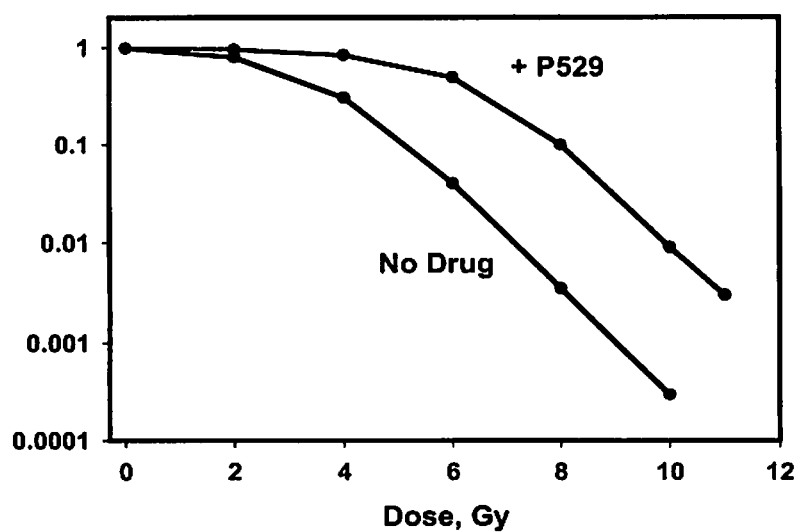
FIG. 1 is a graph showing survival of cultured HOS cells (human osteoblast cells), pretreated with P529 and exposed to gamma radiation.

In accordance with the method of these teachings for mitigating radiation toxicity in a subject the disclosed compounds to be administered include compounds comprising Formula I:

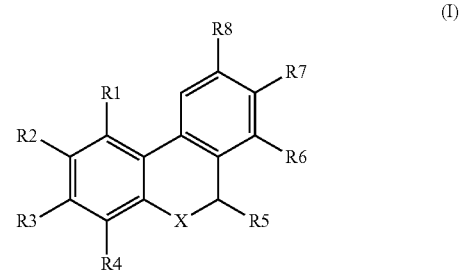

(I)

where,
R1=H or alkyl;
R2=H, OH, O-alkyl, amino, O-heterocyc, O-aryl, O-substituted alkyl, where substitution is e.g. halo, aryl, or heteroaryl, O-Ac, O—PO3, O—SO3, or OSO2NH2;
R3=H, OH, O-alkyl, O—CH2Aryl, O—CH2heteroaryl, O-alkylaryl, O-acyl, or nitro;
R4=H, Alkyl, CH2Aryl, substituted alkyl, OH, O-alkyl, O-aryl, OCH2Aryl, OCH2Heteroaryl, O-Acyl, OPO3, OSO3, or OSO2NH2;
R5=H, Oxo, aryl, hydroxyl, alkyl, or O-alkyl;
R6=H;
R7=H, Acyl, substituted alkyl, where substitution is e.g. hydroxyl or sulfamoyl, alkyl, O-alkyl, or O-substituted alkyl where substitution is O—PO3 or OSO3;
R8=H; and
X=O, N, or S.

In accordance with the method of these teachings for mitigating radiation toxicity in a subject the disclosed compounds to be administered include compounds comprising Formula II:

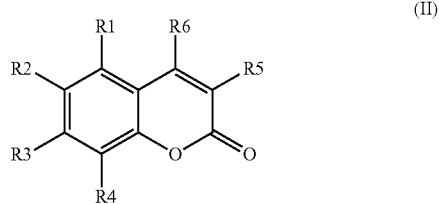

(II)

where,
R1=H or alkyl;
R2=H, O-alkyl, OH, amino, O-heterocyc, O-aryl, O-substituted alkyl where substitution is e.g. halo, aryl, or heteroaryl, O-Ac, O—PO3, O—SO3, or OSO2NH2;
R3=H, O-alkyl, O-substituted alkyl where substitution is aryl or heteroaryl, OH, O-acyl, or nitro;
R4=H, Alkyl, CH2Aryl, substituted alkyl, O), O-alkyl, O-aryl, OCH2Aryl, OCH2Heteroaryl, O-Acyl, OPO3, OSO3, or OSO2NH2;
R5=H, Aryl, heteroaryl or substituted alkyl; and
R6=H, Alkyl, or Aryl.

In accordance with the method of these teachings for mitigating radiation toxicity in a subject the disclosed compounds to be administered include compounds comprising Formula III:

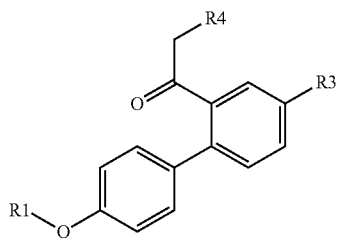

(III)

where,
R1=alkyl or H;
R2=alkyl or H;
R3=Acetyl; and
R4=H or Alkyl.

In accordance with the method of these teachings for mitigating radiation toxicity in a subject the disclosed compounds to be administered include compounds comprising Formula IV:

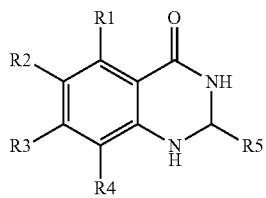

(IV)

where,
R1=H or F;
R2=H or nitro;
R3=H;
R4=H; and
R5=alkyl, substituted alkyl or aryl.

In accordance with the method of these teachings for mitigating radiation toxicity in a subject the disclosed compounds to be administered include compounds comprising benzo[c]chromen-6-one derivatives having the following structure depicted in Table I:

TABLE I

Structural formula of benzo[c]chromen-6-one derivatives

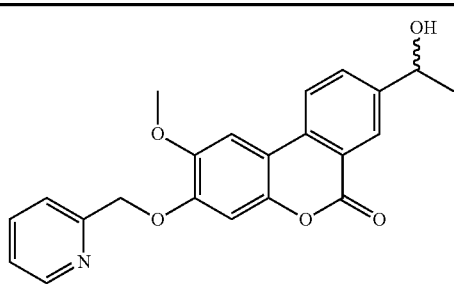

SG00526

TABLE I-continued

Structural formula of benzo[c]chromen-6-one derivatives

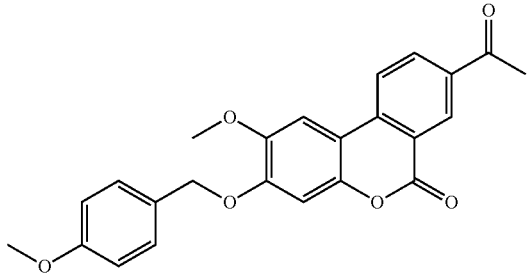 [SMILES: COc1ccc(COc2cc3oc(=O)c4cc(C(C)=O)ccc4c3cc2OC)cc1]

SG00527

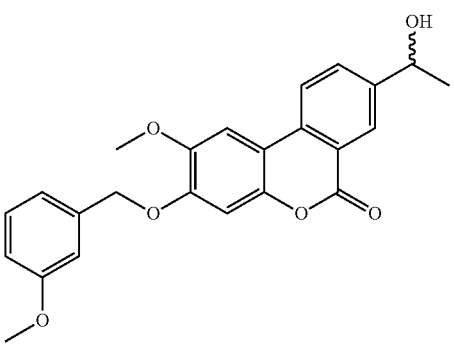 [SMILES: COc1cccc(COc2cc3oc(=O)c4cc(C(C)O)ccc4c3cc2OC)c1]

SG00528

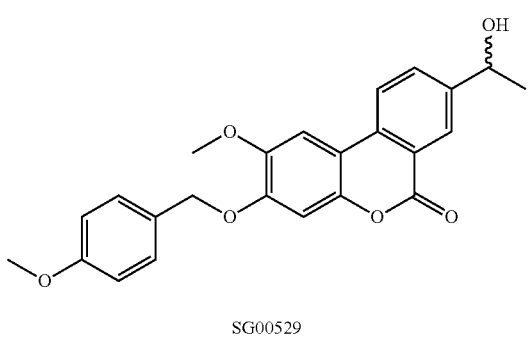

SG00529

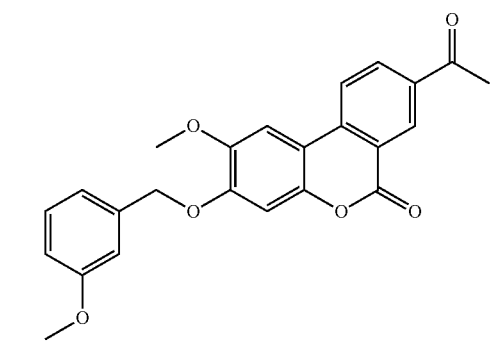 [SMILES: COc1cccc(COc2cc3oc(=O)c4cc(C(C)=O)ccc4c3cc2OC)c1]

SG00530

TABLE I-continued
Structural formula of benzo[c]chromen-6-one derivatives
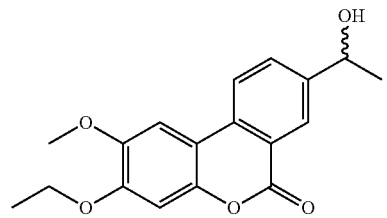 [SMILES: CCOc1cc2oc(=O)c3cc(C(C)O)ccc3c2cc1OC]
SG00531
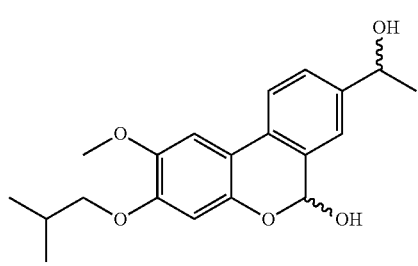 [SMILES: COc1cc2c(cc1OCC(C)C)OC(O)c1cc(C(C)O)ccc1-2]
SG00532
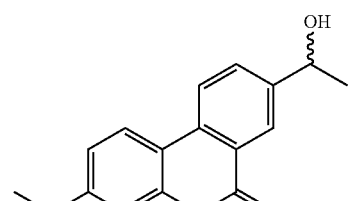
SG00533
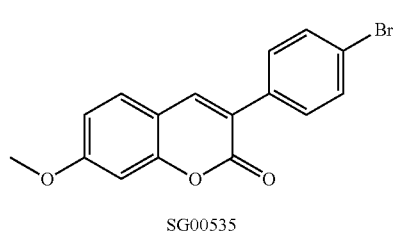
SG00535
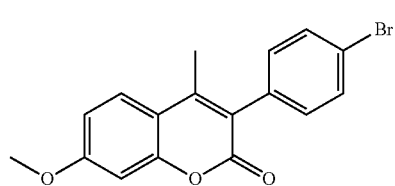 [SMILES: COc1ccc2c(C)c(-c3ccc(Br)cc3)c(=O)oc2c1]
SG00536
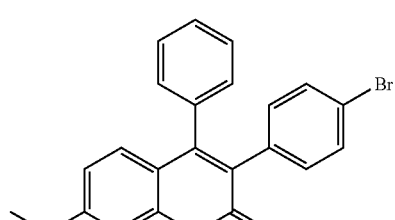
SG00537
TABLE I-continued
Structural formula of benzo[c]chromen-6-one derivatives
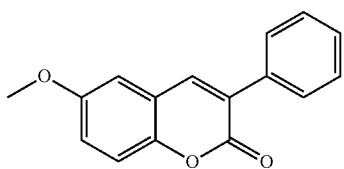 [SMILES: COc1ccc2oc(=O)c(-c3ccccc3)cc2c1]
SG00538
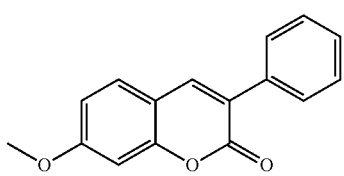 [SMILES: COc1ccc2cc(-c3ccccc3)c(=O)oc2c1]
SG00539
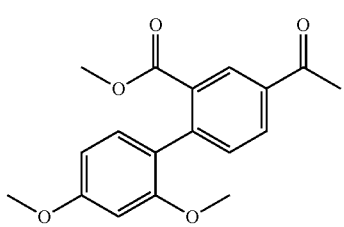 [SMILES: COC(=O)c1cc(C(C)=O)ccc1-c1ccc(OC)cc1OC]
SG00540
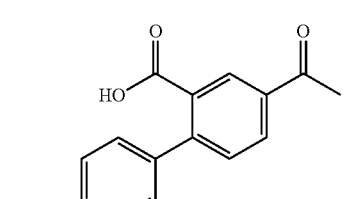
SG00272
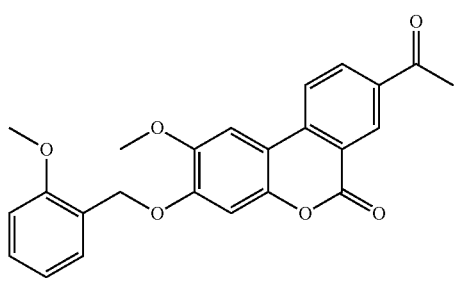 [SMILES: COc1ccccc1COc1cc2oc(=O)c3cc(C(C)=O)ccc3c2cc1OC]
SG00541

TABLE I-continued
Structural formula of benzo[c]chromen-6-one derivatives
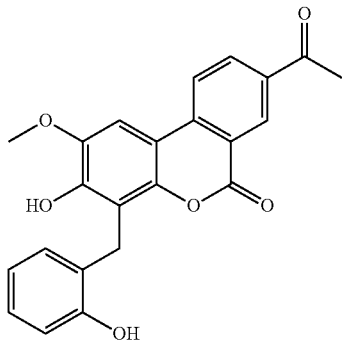 [SMILES: COc1cc2c(oc(=O)c3cc(C(C)=O)ccc32)c(Cc2ccccc2O)c1O]
SG00542
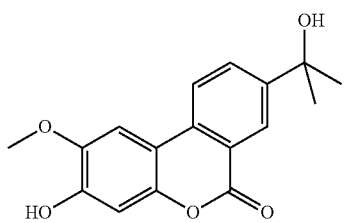 [SMILES: COc1cc2c(cc1O)oc(=O)c1cc(C(C)(C)O)ccc12]
SG00543
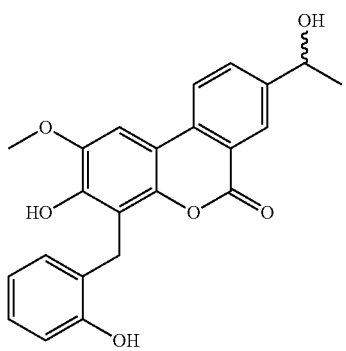 [SMILES: COc1cc2c(oc(=O)c3cc(C(C)O)ccc32)c(Cc2ccccc2O)c1O]
SG00544
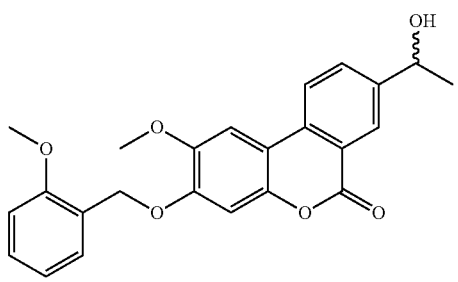 [SMILES: COc1ccccc1COc1cc2oc(=O)c3cc(C(C)O)ccc3c2cc1OC]
SG00545
TABLE I-continued
Structural formula of benzo[c]chromen-6-one derivatives
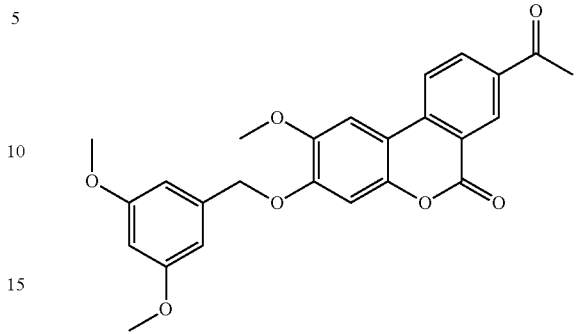
SG00546
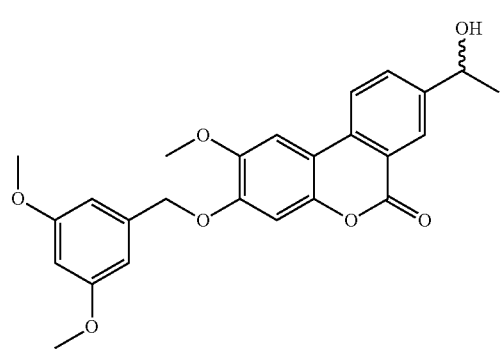 [SMILES: COc1cc(COc2cc3oc(=O)c4cc(C(C)O)ccc4c3cc2OC)cc(OC)c1]
SG00547
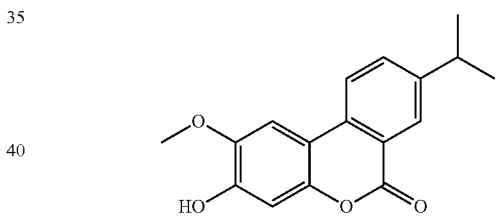
SG00548
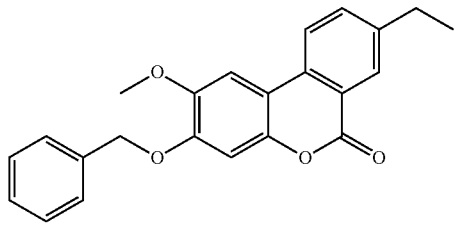 [SMILES: CCc1ccc2c(c1)c(=O)oc1cc(OCc3ccccc3)c(OC)cc12]
SG00549
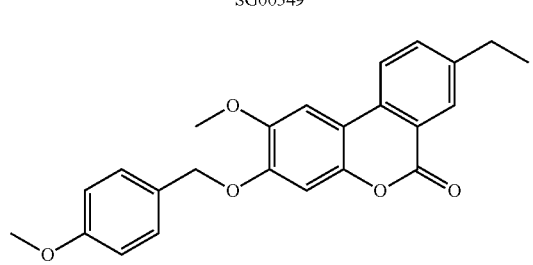
SG00550

TABLE I-continued
Structural formula of benzo[c]chromen-6-one derivatives
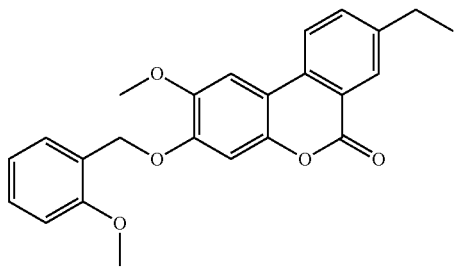 [SMILES: CCc1ccc2c(c1)c(=O)oc1cc(OCc3ccccc3OC)c(OC)cc12]
SG00551
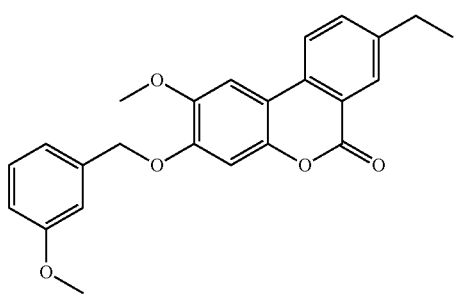 [SMILES: CCc1ccc2c(c1)c(=O)oc1cc(OCc3cccc(OC)c3)c(OC)cc12]
SG00552
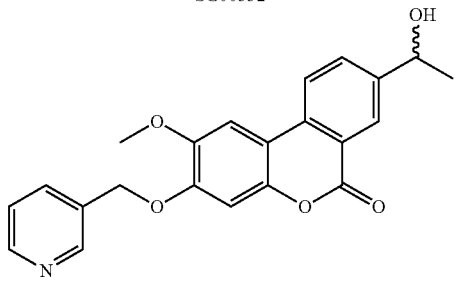
SG00553
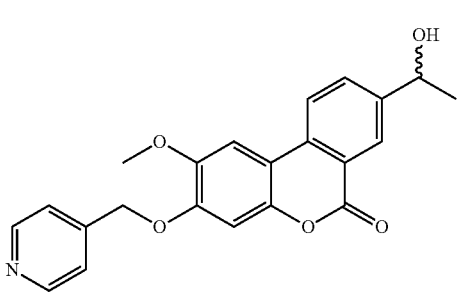 [SMILES: COc1cc2c(cc1OCc1ccncc1)oc(=O)c1cc(C(C)O)ccc12]
SG00554
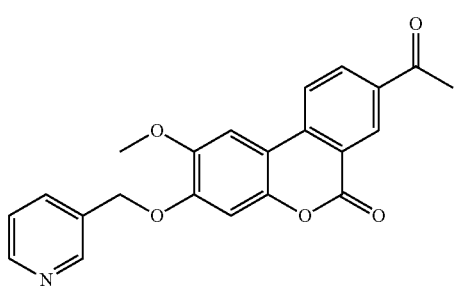 [SMILES: COc1cc2c(cc1OCc1cccnc1)oc(=O)c1cc(C(C)=O)ccc12]
SG00555
TABLE I-continued
Structural formula of benzo[c]chromen-6-one derivatives
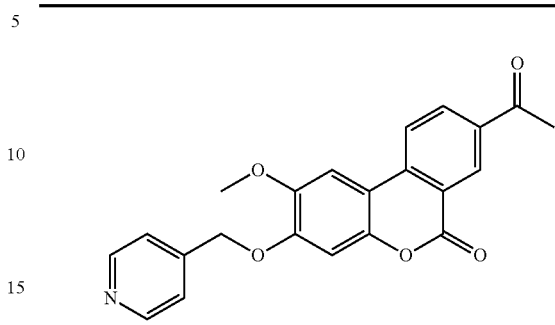
SG00556
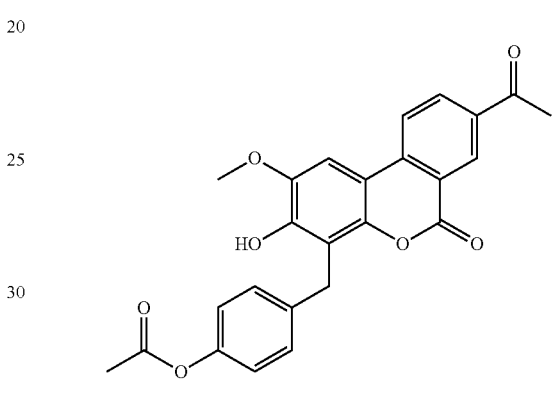
SG00557
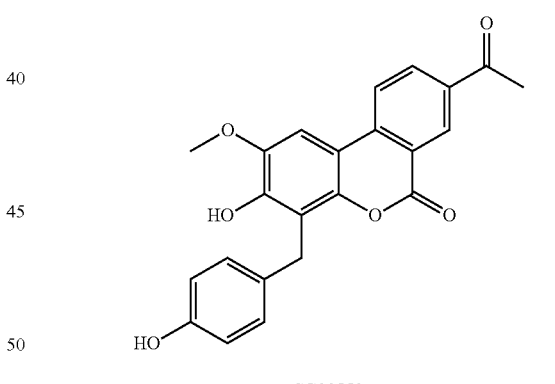
SG00558
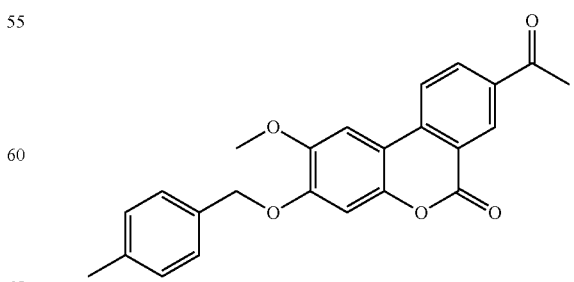
SG00559

TABLE I-continued
Structural formula of benzo[c]chromen-6-one derivatives
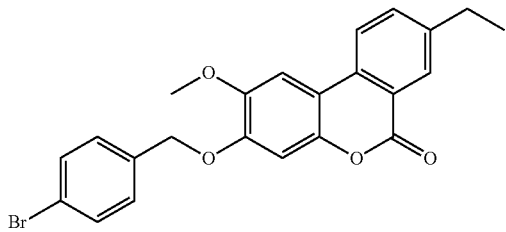
SG00560
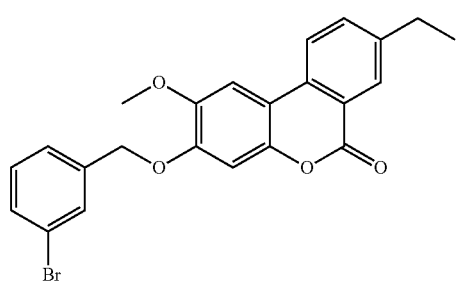 [SMILES: CCc1ccc2c(c1)c(=O)oc1cc(OCc3cccc(Br)c3)c(OC)cc12]
SG00561
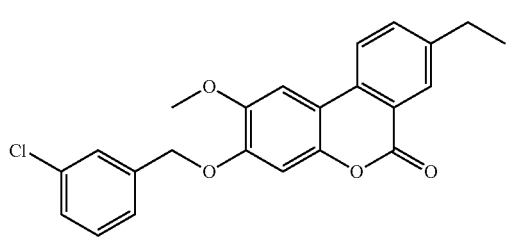 [SMILES: CCc1ccc2c(c1)c(=O)oc1cc(OCc3cccc(Cl)c3)c(OC)cc12]
SG00562
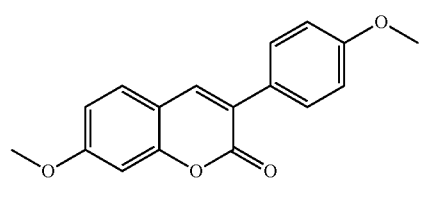
SG00563
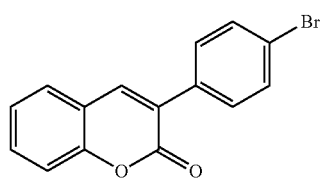 [SMILES: O=c1oc2ccccc2cc1-c1ccc(Br)cc1]
SG00564
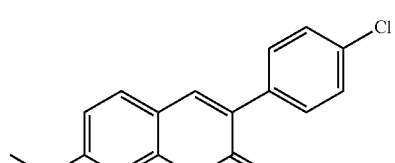
SG00565
TABLE I-continued
Structural formula of benzo[c]chromen-6-one derivatives
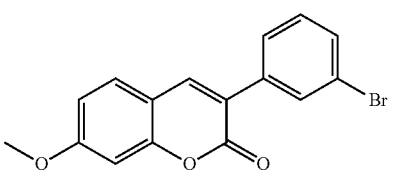 [SMILES: COc1ccc2cc(-c3cccc(Br)c3)c(=O)oc2c1]
SG00566
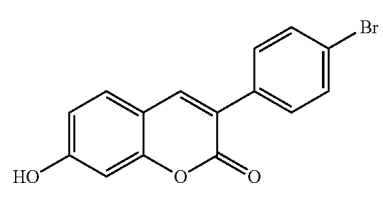 [SMILES: O=c1oc2cc(O)ccc2cc1-c1ccc(Br)cc1]
SG00567
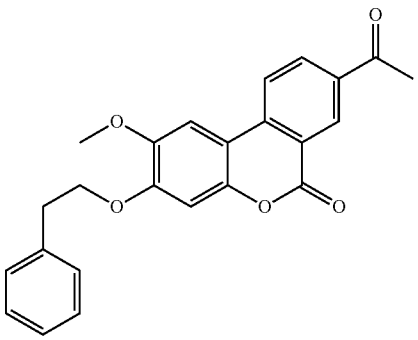 [SMILES: COc1cc2c(cc1OCCc1ccccc1)oc(=O)c1cc(C(C)=O)ccc12]
SG00568
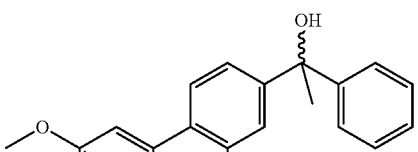
SG00569
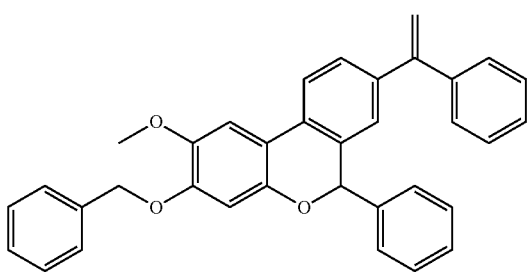 [SMILES: C=C(c1ccccc1)c1ccc2c(c1)C(c1ccccc1)Oc1cc(OCc3ccccc3)c(OC)cc1-2]
SG00570

TABLE I-continued
Structural formula of benzo[c]chromen-6-one derivatives
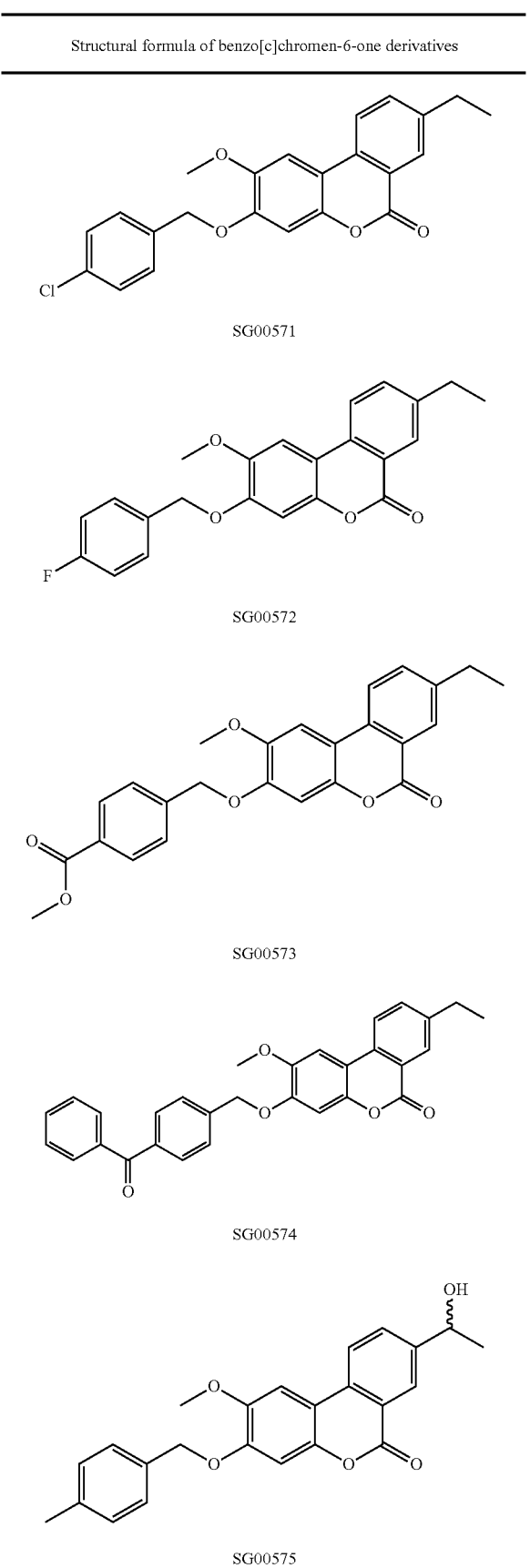
SG00571
SG00572
SG00573
SG00574
SG00575
TABLE I-continued
Structural formula of benzo[c]chromen-6-one derivatives
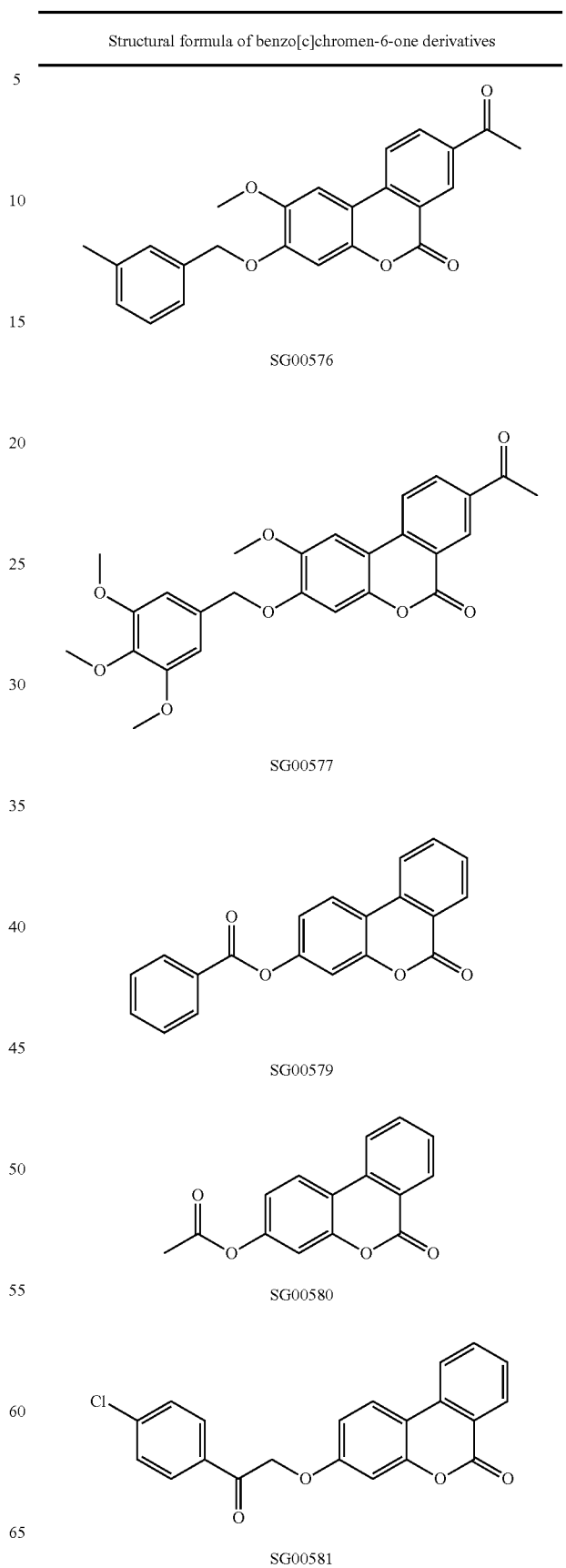
SG00576
SG00577
SG00579
SG00580
SG00581

TABLE I-continued
Structural formula of benzo[c]chromen-6-one derivatives
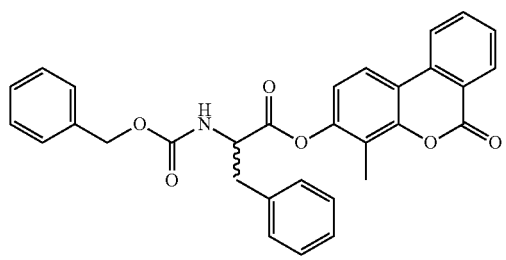 [SMILES: Cc1c(OC(=O)C(Cc2ccccc2)NC(=O)OCc2ccccc2)ccc2c1oc(=O)c1ccccc12]
SG00582
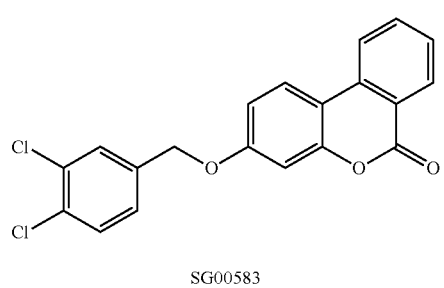
SG00583
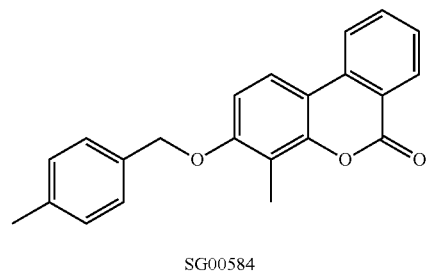
SG00584
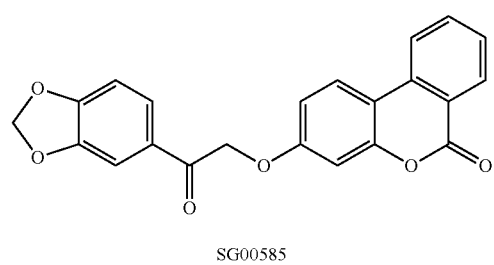
SG00585
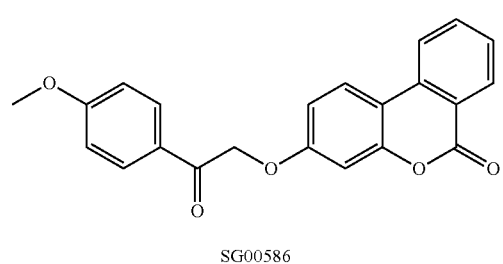
SG00586
TABLE I-continued
Structural formula of benzo[c]chromen-6-one derivatives
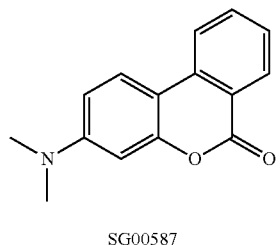
SG00587
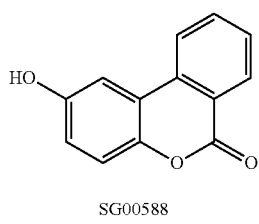
SG00588
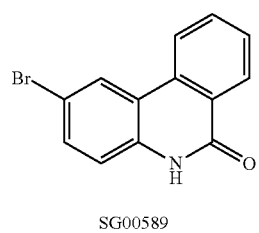
SG00589
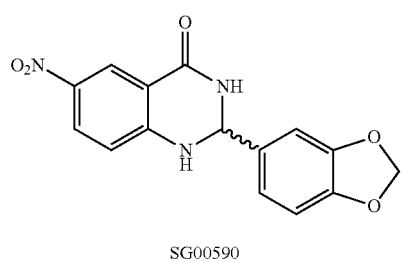
SG00590
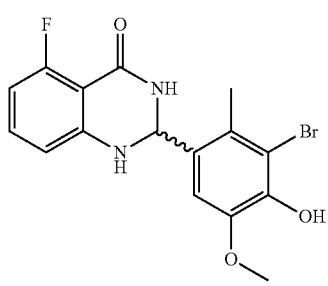 [SMILES: COc1cc(C2NC(=O)c3c(F)cccc3N2)c(C)c(Br)c1O]
SG00591
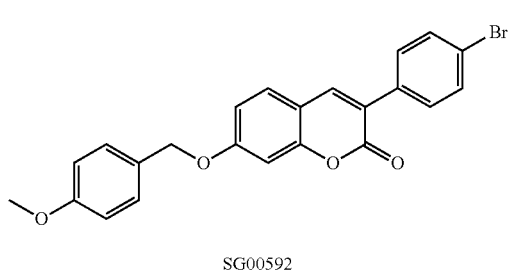
SG00592

TABLE I-continued
Structural formula of benzo[c]chromen-6-one derivatives
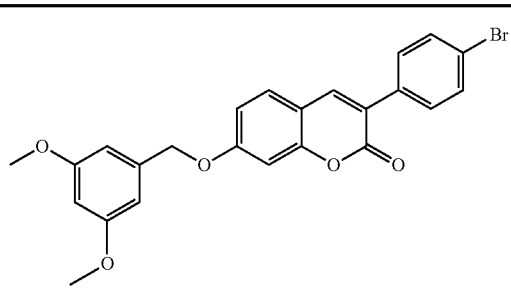
SG00593
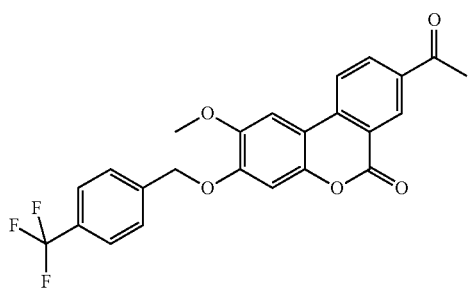 [SMILES: COc1cc2c(cc1OCc1ccc(C(F)(F)F)cc1)oc(=O)c1cc(C(C)=O)ccc12]
SG00594
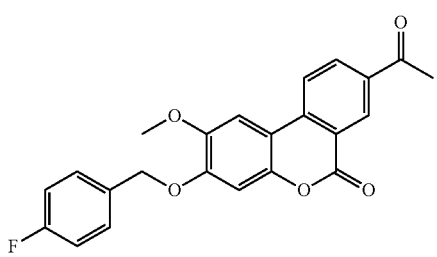 [SMILES: COc1cc2c(cc1OCc1ccc(F)cc1)oc(=O)c1cc(C(C)=O)ccc12]
SG00595
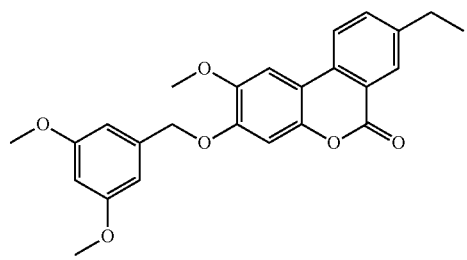 [SMILES: CCc1ccc2c(c1)c(=O)oc1cc(OCc3cc(OC)cc(OC)c3)c(OC)cc12]
SG00596
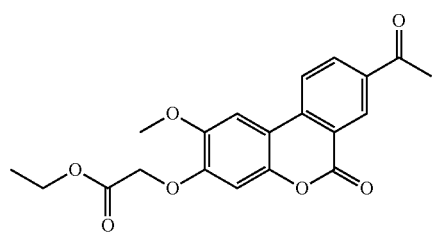 [SMILES: CCOC(=O)COc1cc2oc(=O)c3cc(C(C)=O)ccc3c2cc1OC]
SG00597
TABLE I-continued
Structural formula of benzo[c]chromen-6-one derivatives
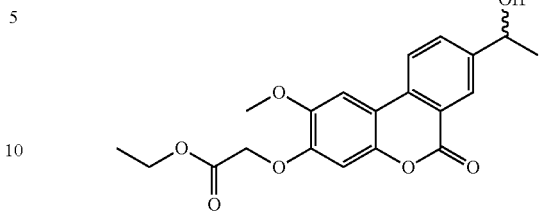
SG00598
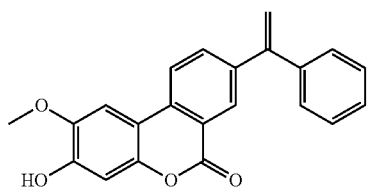 [SMILES: C=C(c1ccccc1)c1ccc2c(c1)c(=O)oc1cc(O)c(OC)cc12]
SG00599
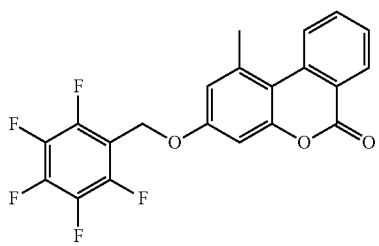 [SMILES: Cc1cc(OCc2c(F)c(F)c(F)c(F)c2F)cc2oc(=O)c3ccccc3c12]
SG00600
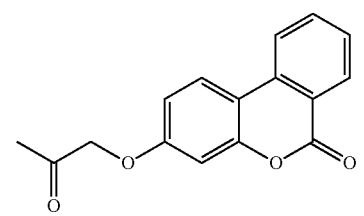 [SMILES: CC(=O)COc1ccc2c(c1)oc(=O)c1ccccc12]
SG00601
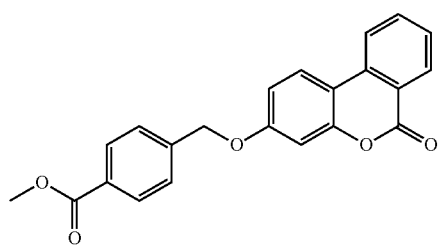 [SMILES: COC(=O)c1ccc(COc2ccc3c(c2)oc(=O)c2ccccc23)cc1]
SG00602
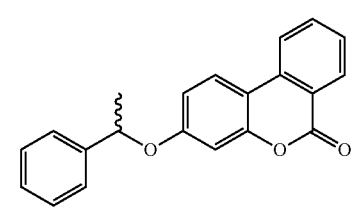 [SMILES: CC(Oc1ccc2c(c1)oc(=O)c1ccccc12)c1ccccc1]
SG00603

TABLE I-continued
Structural formula of benzo[c]chromen-6-one derivatives
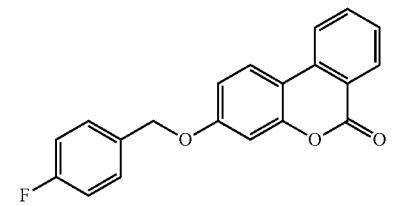 [SMILES: O=c1oc2cc(OCc3ccc(F)cc3)ccc2c2ccccc12]
SG00604
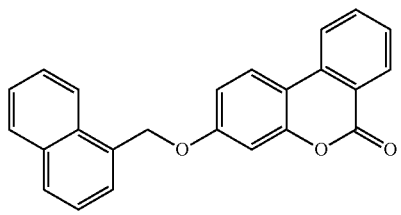 [SMILES: O=c1oc2cc(OCc3cccc4ccccc34)ccc2c2ccccc12]
SG00605
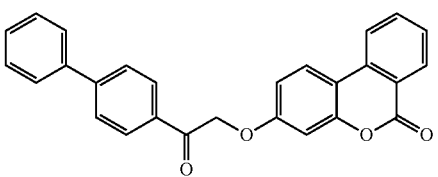 [SMILES: O=C(COc1ccc2c(c1)oc(=O)c1ccccc12)c1ccc(-c2ccccc2)cc1]
SG00606
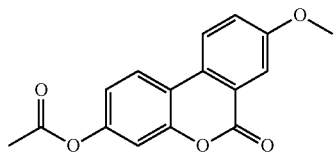 [SMILES: COc1ccc2c(c1)c(=O)oc1cc(OC(C)=O)ccc12]
SG00607
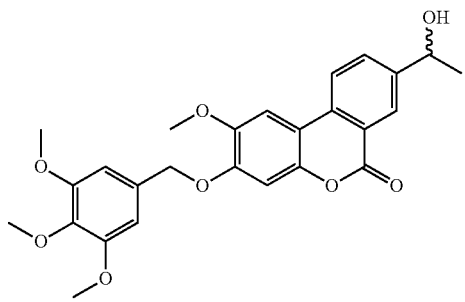 [SMILES: COc1cc2c(cc1OCc1cc(OC)c(OC)c(OC)c1)oc(=O)c1cc(C(C)O)ccc12]
SG00609
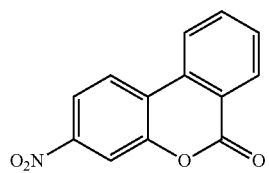 [SMILES: O=c1oc2cc([N+](=O)[O-])ccc2c2ccccc12]
SG00610
TABLE I-continued
Structural formula of benzo[c]chromen-6-one derivatives
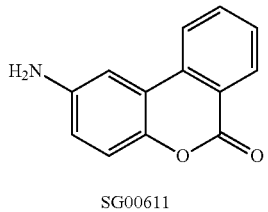
SG00611
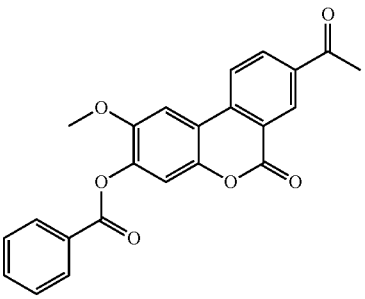 [SMILES: COc1cc2c(cc1OC(=O)c1ccccc1)oc(=O)c1cc(C(C)=O)ccc12]
SG00612
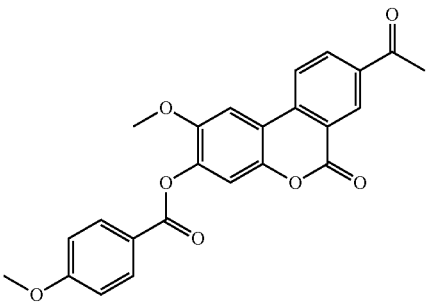 [SMILES: COc1ccc(C(=O)Oc2cc3oc(=O)c4cc(C(C)=O)ccc4c3cc2OC)cc1]
SG00613
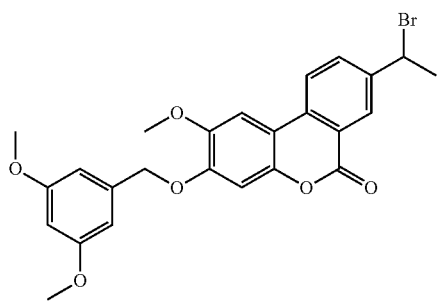 [SMILES: COc1cc(COc2cc3oc(=O)c4cc(C(C)Br)ccc4c3cc2OC)cc(OC)c1]
SG00614
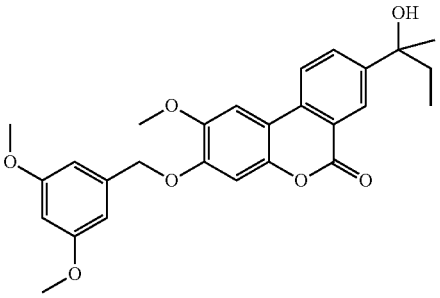 [SMILES: CCC(C)(O)c1ccc2c(c1)c(=O)oc1cc(OCc3cc(OC)cc(OC)c3)c(OC)cc12]
SG00615

TABLE I-continued

Structural formula of benzo[c]chromen-6-one derivatives

SG00616

SG00617

SG00618

SG00619

SG00620

TABLE I-continued

Structural formula of benzo[c]chromen-6-one derivatives

SG00273

SG00393

SG00477

SG00519

SG00292

SG00629

The individual benzo[c]-chromen-6-one derivatives of Table I are identified by the designation "SG" followed by a number. They are alternatively referred to herein by the designation "Palomid" or simply "P" followed by the same number, i.e. the terms "SG", "Palomid" and "P" are used interchangeably throughout this application.

In accordance with the method of these teachings for mitigating radiation toxicity in a subject the disclosed compounds to be administered can be formulated as pharmaceutical compositions comprising benzo[c]chromen-6-one derivatives together with a pharmaceutical acceptable carrier, diluent or excipient.

"Alkyl" as used herein may include a saturated or unsaturated hydrocarbon moiety, preferably saturated, e.g., one to eight, e.g., one to six, e.g., one to four carbon atoms in length, which may be linear or branched (e.g., n-butyl or tert-butyl) unless otherwise specified, and may be optionally substituted, e.g., mono-, di-, or tri-substituted on any one of the carbon atoms, e.g., with $C_{1-4}$ alkyl (e.g., methyl), $C_{1-4}$ alkoxy, halogen (e.g., chloro or fluoro), halo$C_{1-4}$ alkyl (e.g., trifluoromethyl), hydroxy, and carboxy. Examples of alkyl include, but are not limited to, methyl, ethyl, n-propyl, i-propyl, n-butyl, i-butyl, sec-butyl, t-butyl, 3-methylpentyl, 4-methylpentyl, n-pentyl, n-hexyl and n-heptyl.

"Aryl" as used herein may include a monocyclic or polycyclic aromatic hydrocarbon, preferably phenyl, optionally substituted, e.g., with $C_{1-4}$ alkyl (e.g., methyl), $C_{1-4}$ alkoxy, halogen (e.g., chloro or fluoro), halo$C_{1-4}$ alkyl (e.g., trifluoromethyl), hydroxy, carboxy, or an additional aryl or heteroaryl.

As used herein, the term "DRF" ("dose reduction factor") is the ratio of radiation doses required to produce the same biologic effect in the absence and presence of the radioprotectant.

By "effective amount" it is meant a therapeutically effective amount that relieves symptoms, partially or completely, associated with a particular disease or syndrome. Such amounts can be readily determined by an appropriately skilled practitioner, taking into account the condition to be treated, the route of administration, and other relevant factors—well known to those skilled in the art. Such a person will be readily able to determine a suitable dose, mode and frequency of administration.

Though it is not possible to specify a single predetermined pharmaceutically effective amount of the compounds of the invention, and/or their pharmaceutical compositions, for each and every disease condition to be treated, determining such pharmaceutically effective amounts are within the skill of, and ultimately at the discretion of an attendant physician or clinician of ordinary skill. In some embodiments, the active compounds of the invention are administered to achieve peak plasma concentrations of the active compound of from typically about 0.1 to about 1000 µM, about 1 to 50 µM, about 2 to 30 µM, about 1 to 10 µM, about 1 to 100 µM, about 1 to 500 µM, or 1 to 750 µM. This can be achieved, for example, by the intravenous injection of a 0.05 to 5% solution of the active ingredient, optionally in saline, or orally administered as a bolus containing about 0.5-500 mg of the active ingredient. Desirable blood levels can be maintained by continuous infusion to provide about 0.01-500 mg/kg/hr, 0.1-100 mg/kg/hr, 1-50 mg/kg/hr, 5-10 mg/kg/hr, or 0.01-5.0 mg/kg/hr and/or by intermittent infusions containing about 0.1-1000 mg/kg, 0.5-500 mg/kg, 1-400 mg/kg, 10-400 mg/kg, or 0.4-15 mg/kg of the active compounds of the invention.

Pharmaceutically acceptable salts of the benzo[c]chromen-6-one derivatives or prodrugs thereof may be prepared in any conventional manner. In vivo hydrolysable esters, for example, methyl esters, phosphate or sulfate groups, and amides or carbamates may be prepared in any conventional manner.

The benzo[c]chromen-6-one derivatives or prodrugs thereof can be provided as physiologically acceptable formulations using known techniques and these formulations can be administered by standard routes. The compositions may be administered through means including, but not limited to, topical, oral, rectal or parenteral, for example, intravenous, subcutaneous or intramuscular, route. In addition, the compositions may be incorporated into formats allowing for sustained release, the formats being implanted in the proximity of where the delivery is desired, for example, at the site of the skin disease or aging skin or in the vicinity of aberrant vasculature. The dosage of the composition will depend on the condition being treated, the particular derivative used, and other clinical factors such as weight and condition of the subject and the route of administration of the compound—all of which is appreciated by those skilled in the art. For example, a person skilled in the art will be able by reference to standard texts, such as Remington's Pharmaceuticals Sciences $17^{th}$ edition (the entire teaching of which is incorporated herein by reference), determine how the formulations are to be made and how these may be administered.

The formulations including, but not limited to, those suitable for oral, rectal, nasal, inhalation, topical (including, but not limited to, dermal, transdermal, buccal and sublingual), vaginal or parenteral (including, but not limited to, subcutaneous, intramuscular, intravenous, intradermal, intraocular (including, but not limited to, intra-vitreal, sub-conjunctival, sub-Tenon's, trans-scleral), intra-tracheal and epidural) and inhalation administration. The formulations may be conveniently presented in unit dosage form and may be prepared by conventional pharmaceutical techniques. Such techniques include the step of bringing into association the active ingredient and a pharmaceutical carrier(s) or excipient(s). The formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil emulsion, etc.

A tablet may be made by compression or molding, optimally with one or more accessory ingredient. Compressed tablets may be prepared by compressing, in a suitable machine, the active ingredient in a free-flowing form such as a powder or granules, optionally mixed with a binder, lubricant, inert diluent, preservative, surface-active or dispersing agent. Molded tablets may be made by molding, in a suitable machine, a mixture of the powdered compound moistened with an inert liquid diluent. The tablets may optionally be coated or scored and may be formulated so as to provide a slow or controlled release of the active ingredient therein.

Formulations suitable for administration via the mouth include lozenges comprising the ingredients in a flavored basis, usually sucrose and acacia or tragacanth; pastilles comprising the active ingredient in an inert basis such as gelatin and glycerin, or sucrose and acacia; and mouthwashes comprising the ingredient to be administered in a suitable liquid carrier.

Formulations suitable for topical administration to the skin may be presented as ointments, creams, gels and pastes comprising the ingredient to be administered in a pharmaceutical, cosmeceutical or cosmetic acceptable carrier. A viable delivery system is a transdermal patch containing the ingredient to be administered.

Formulations for rectal administration may be presented as a suppository with a suitable base comprising, for example, cocoa butter or a salicylate.

Formulations suitable for nasal administration, wherein the carrier is a solid, include a coarse powder having a particle size, for example, in the range of 20 to 500 microns which is administered in the manner in which snuff is taken, for example, by rapid inhalation through the nasal passage from a container of the powder held close up to the nose. Suitable formulations include wherein the carrier is a liquid for administration, as for example a nasal spray or as nasal drop, including aqueous or oily solutions of the active ingredient.

Formulations suitable for vaginal administration may be presented as pessaries, tampons, creams, gels, pastes, foams or spray formulations containing, in addition to the active ingredient, ingredients such as carriers as are known in the art to be appropriate.

Formulation suitable for inhalation may be presented as mists, dusts, powders or spray formulations containing, in addition to the active ingredient, ingredients such as carriers as are known in the art to be appropriate.

Formulations suitable for parenteral administration include aqueous and non-aqueous sterile injection solutions which may contain anti-oxidants, buffers, bacteriostatic agents and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried, lyophilized, conditions requiring only the addition of the sterile liquid, for example, water for injections, immediately prior to use. Extemporaneous injection solution and suspensions may be prepared from sterile powders, granules and tablets of the kinds previously described.

When desired, the above-described compositions can be adapted to provide sustained release of the active ingredient employed, e.g., by combination thereof with certain hydrophilic polymer matrices, e.g., comprising natural gels, synthetic polymer gels or mixtures thereof.

Acceptable unit dosage formulations are those containing a daily dose or unit, daily sub-dose, as herein above recited, or an appropriate fraction thereof, of the administered ingredient.

In addition to the ingredients mentioned above, the formulations of the present invention may include other agents conventional in the art having regard to the type of formulation in question, for example, those suitable for oral administration may include flavoring agents.

Disclosed herein are methods of treating radiation damage. Ionizing radiation (IR) remains a main stream therapy for cancer, since it controls both primary and metastatic cancer without significant systemic damage. However, radiation therapy does cause IR-induced local damage of normal tissue (radiation toxicity), leading to a temporary or persistent impairment of irradiated tissues, which lowers the life quality of cancer patients. Some severe side effects such as the acute radiation syndrome conditions of gastrointestinal syndrome and bone marrow syndrome can even result in the discontinuation of the life-saving radiation therapy (Johansen et al. Radiother Oncol. 40:101-9 (1996), Nierrierko et al. IntJRadiat Oncol Biol Phys. 25:135-45 (1993), Wiess et al. Toxicology 15:189(1-2):1-20 (2003). Radiation damage can also occur by exposure to nuclear radiation, or exposure to a weapon that causes radiation. As used herein, "weapon" is meant any bomb, machine, or other device capable of being used in conventional warfare, nonconventional warfare, or terrorist activities.

Disclosed herein are methods of reducing radiation damage in a subject by administering to the subject an effective amount of an analogue or derivative of benzo[c]chromen-6-one or other compositions disclosed herein. As disclosed above, the radiation damage can be caused by radiation therapy, such as that used to treat cancer. The radiation damage can also be caused by nuclear radiation, or by a weapon, such as a bomb or other terrorist agent. The compositions disclosed herein can be administered prior to, after, or during exposure to radiation. Thus, disclosed herein are methods of treating, inhibiting, preventing, or mitigating radiation toxicity, radiation induced gastrointestinal (GI) syndrome or bone marrow (BM) syndrome, acute radiation syndrome (ARS), lethal brain bleeding, or the effects associated with any of the above conditions. The disclosed compositions can be administered one, two, three or four times every 24 hours.

As used herein, a "decrease" can refer to any change that results in a smaller amount of a symptom, condition, or disease such as radiation toxicity. Thus, a "decrease" can refer to a reduction in an activity as well as a reduction in the effects of a disease or condition. Also, for example, a decrease can be a change in the symptoms of a disorder such that the symptoms are less than previously observed. Thus, for example, a decrease in the toxic effects of ionizing radiation can include but is not limited to a 10%, 20%, 30%, 40%, 50%, 60%, 70%, 80%, 90% or 100% decrease in the symptoms associated with exposure to ionizing radiation.

As used herein, an "increase" can refer to any change that results in a larger amount of a symptom, condition, or disease such as radiation toxicity. Thus, for example, an increase in the amount in toxic effects of ionizing radiation can include but is not limited to a 10%, 20%, 30%, 40%, 50%, 60%, 70%, 80%, 90% or 100% increase in the symptoms associated with exposure to ionizing radiation.

As used herein, "mitigate" means to reduce the damage associated with a symptom, disease, or condition relative to the untreated state. It is also understood that "mitigation" can be in reference to a symptom, disease, or condition, in addition to or alternatively to damage associated with the symptom, disease, or condition. It is understood and herein contemplated that the reduction is not limited to the complete ablation of the damage, symptom, disease, or condition, but may include, for example, a 10% reduction in the activity, response, condition, or disease as compared to the native or control level. Thus, the reduction can be a 10, 20, 30, 40, 50, 60, 70, 80, 90 100%, or any amount of reduction in between as compared to untreated, native, or control levels. It is also understood that "mitigation" has occurred if the further damage due to disease progression or symptoms are reduced without a reduction in the state prior to treatment. Thus, for example, in a subject with damage from radiation toxicity prior to treatment, the radiation toxicity would be "mitigated" if, following treatment, further damage from progression of toxicity was reduced relative to a control, even if the level of damage in the subject was not reduced relative to pretreatment levels. By way of example, if a subject had a radiation toxicity damage at a level of X when treatment was started, a composition or treatment method would be understood to mitigate the damage from radiation toxicity even if the damage from radiation toxicity increased (e.g., X+10%, 20%, 30%, 40%, 50%, 60%, 70%, 80%, 90%) provided untreated controls increased more (e.g., X+15%, 25%, 35%, 45%, 55%, 65%, 75%, 85%, 95%).

"Inhibit", "inhibiting" and "inhibition" mean to decrease an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

"Treatment", "treat", or "treating" mean a method of reducing the effects of a disease or condition. Treatment can also refer to a method of reducing the disease or condition itself rather than just the symptoms. The treatment can be any reduction from native levels and can be but is not limited to the complete ablation of the disease, condition, or the symptoms of the disease or condition. Therefore, in the disclosed methods, "treatment" can refer to a 10%, 20%, 30%, 40%, 50%, 60%, 70%, 80%, 90%, or 100% reduction in the severity of an established disease or the disease progression. For example, a disclosed method for reducing the effects of radiation toxicity, gastrointestinal syndrome, bone marrow syndrome, inflammation, or uncontrolled cellular proliferation is considered to be a treatment if there is a 10% reduction in one or more symptoms of the disease in a subject with the disease when compared to native levels in the same subject or control subjects. Thus, the reduction can be a 10, 20, 30, 40, 50, 60, 70, 80, 90, 100%, or any amount of reduction in between as compared to native or control levels. It is understood and herein contemplated that "treatment" does not necessarily refer to a cure of the disease or condition, but an improvement in the outlook of a disease or condition.

"Cytoprotective agents" include compounds which provide protection to cells against harmful agents, particularly compounds which provide protection from radiation. Such compounds may include antibiotics, blood products (platets, blood plasma, red blood cells and/or whole blood), colony stimulating factors, granulocyte colony stimulating factor, stem cells, and/or steroids. Such compounds are well known in the art. Cytoprotective agents may also include radioprotectants, compounds which have previously been utilized to reduce damage when a subject is exposed to radiation, such as potassium iodide, DTPA, 5-AED, neutraceuticals, and amifostine.

An Akt inhibitor, 8-(1-Hydroxy-ethyl)-2-methoxy-3-(4-methoxy-benzyloxy)-benzo[c]chromen-6-one, (Palomid 529 or P529) has been shown to have antitumour efficacy in a prostate cell model (Riaz). Pharmacologic approaches using AKT inhibitors have shown that they can afford endothelial cell protection in vitro and in vivo through a mechanism involving AKT and 7-pass transmembrane receptors coupled to Gi proteins.

P529 was tested for activity as a radioprotector in vivo, to evaluate its capability as an inhibitor of radiation-induced leukemia, and to assess its ability to protect chromosomes from radiation damage.

Example I

Cellular Radioprotection by P529

Experimental Design:
Radiation protection by P529 is evaluated using a human osteoblast cell model (HOS cells). The effect of P529 (10 μM, 4 hr) on cell survival after radiation is assessed; cell survival was measured using the colony formation assay.

Experimental Results:
As shown in FIG. 1, when cultured HOS cells are exposed to gamma radiation, a dose-dependent decrease in cell survival is observed. However, when cells are pretreated with P529 10 μM for 4 hr prior to radiation exposure, they exhibited significant radiation resistance. A comparison of cell survival with and without P529 (under these conditions) indicates a dose-reduction factor (DRF) of 1.38 (at the 0.005 survival fraction).

Figure 2:
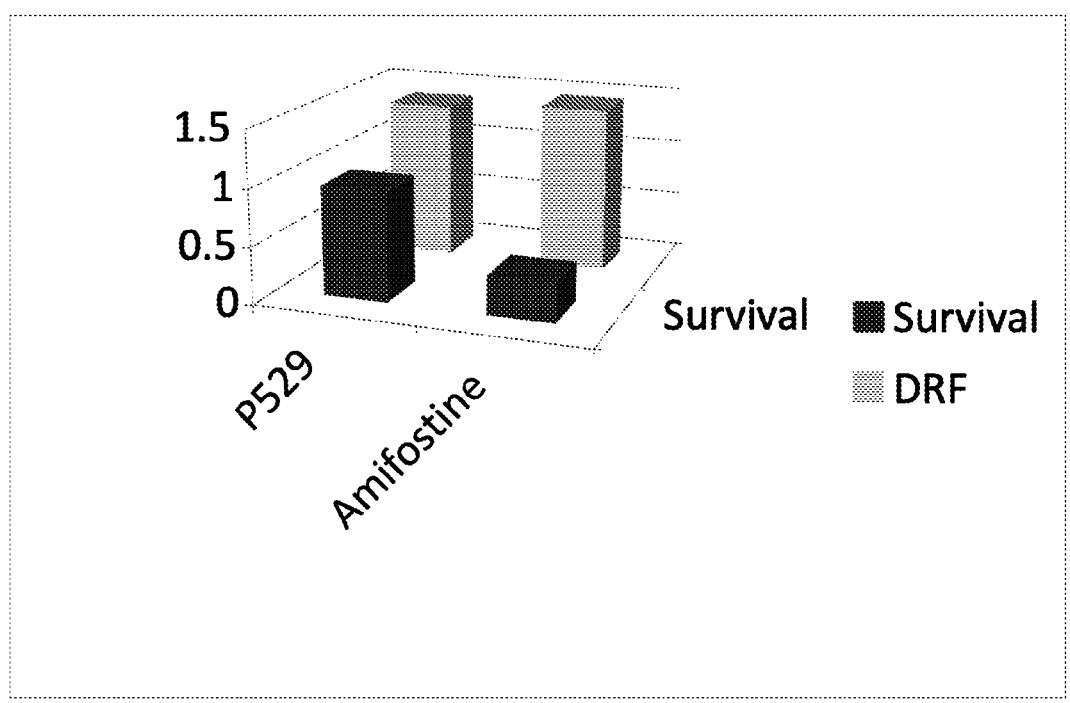
FIG. 2 is a bar graph showing survival and DRF (dose reduction factor) of cultured HOS cells, pre-treated with P529 or amifostine and exposed to gamma radiation.
Figure 3:
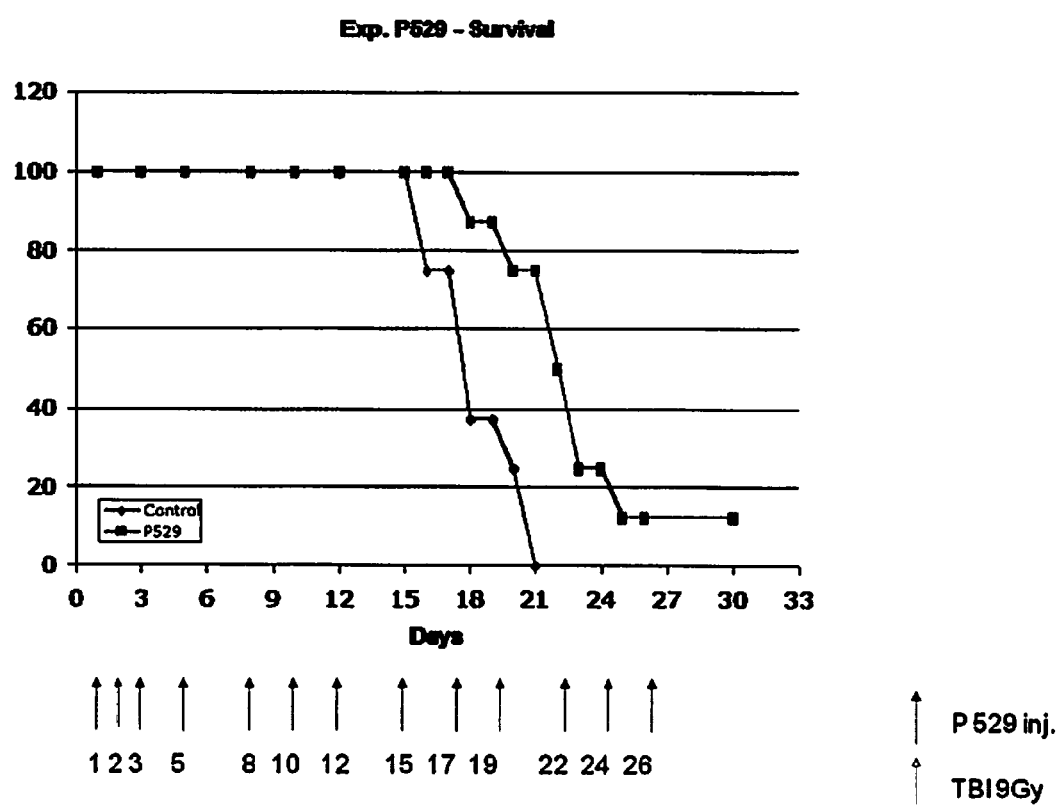
FIG. 3 is a graph showing survival of C57 mice treated with P529 and exposed to gamma radiation.
Figure 4:
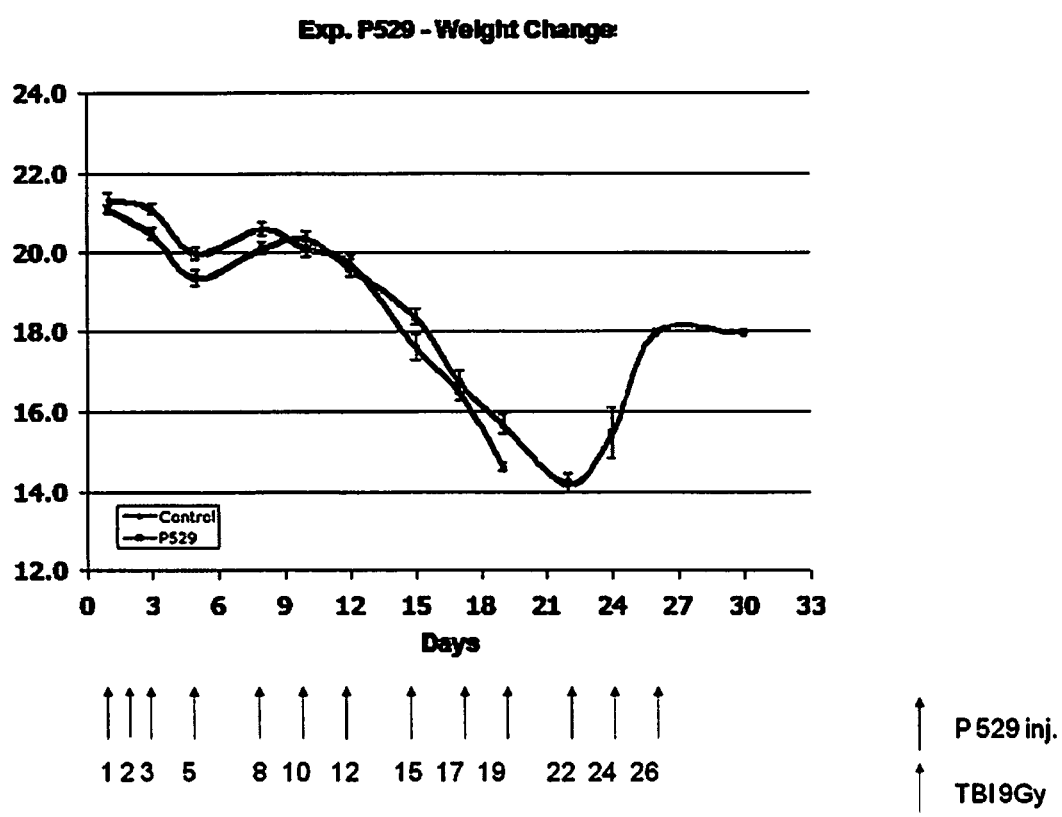
FIG. 4 is a graph showing weight changes of C57 mice treated with P529 and exposed to gamma radiation.

A comparison to amifostine is done and the data is shown in FIG. 2. While the DRF for amifostine (1.45) is slightly greater than for P529 (1.34) in vitro, the significantly increased survival P529 (0.99) versus amifostine (0.35) under radioprotective treatment conditions indicates that p529 is a significantly more favorable radioprotectant.

Example II

Chromosomal Radiation Protection by P529

Experimental Design:
Non-tumorigenic immortalized human osteosarcoma cells (HOS) are exposed to increasing doses of gamma radiation (O-4 Gy; 6.6 Gy/min). Control cells receive no drug; Drug-treated cells receive P529 (25 uM, 12 hrs pre-radiation). Metaphase plates are prepared from control and drug-treated cells (Gupta, Br J Radiol, 59:625 1986). A total of 100 metaphases are examined per group/dose. Aberrant metaphases, chromatid and chromosome breaks, fragments, rings, and dicentrics are scored under a light microscope. Aberrations are identified using criteria given by Savage (J Med Genetics 12:103-122, 1976).

TABLE 2

| | Radiation Alone | | | | Radiation + P529 | | | |
|---|---|---|---|---|---|---|---|---|
| Dose (Gy) | Percent Aberrant Cells | Fragments | Breaks | Rings + Dicentrics | Percent Aberrant Cells | Fragments | Breaks | Rings + Dicentrics |
| 0 | .66 ± 0.055 | .007 ± 0.0008 | .0019 ± .002 | .0006 ± — | .66 ± .07 | .007 ± .0009 | .0016 ± .0002 | 0.00 ± 0.0 |
| 1 | 5.9 ± 0.61 | .11 ± 0.01 | .002 ± .0002 | .0013 ± .0002 | 3.1 ± .033 | .05 ± .006 | .0013 ± .0002 | 0.00 ± 0.0 |
| 2 | 14.4 ± 1.22 | .3 ± 0.033 | .006 ± .0007 | .0129 ± .002 | 5.0 ± .052 | .118 ± .022 | .0018 ± .0002 | .003 ± .0004 |
| 3 | 28.5 ± 2.15 | .61 ± 0.05 | .0105 ± .002 | .0279 ± .003 | 11.4 ± 1.22 | .23 ± .028 | .0022 ± .0003 | .005 ± .0004 |
| 4 | 55.5 ± 5.58 | 1.1 ± 0.12 | .016 ± .002 | .0356 ± .004 | 19.5 ± 1.29 | .30 ± .031 | .0039 ± .0004 | .017 ± .002 |

Experimental Results:
The data demonstrate that P529 can provide chromosomal protection from radiation exposure in human HOS cells. See Table 2.
The data shows that P529 is a radiation protector showing activity against acute radiation damage in vitro.

Example III

Mitigation Radiation Effect by P529 in vivo

Experimental Design:

Sixteen female C57 mice are exposed to gamma radiation (9 Gy). Group 1 received radiation only (no drug). Group 2 received radiation and P529 as noted in the following schedule:

Schedule:
Day 1—P529 inj ip 100 μl
Day 2—TBI 9Gy
Days 3, 5, 8, 10, 12, 15, 17, 19, 22, 24, 26—P529 inj ip 100 μl Experimental Results:

The data demonstrate that P529 can mitigate the radiation effect, and damage caused by radiation.

That which is claimed:

1. A method for reducing radiation damage, reducing potential damage by exposure to radiation, treating damage caused by exposure to radiation, and/or inhibiting formation of damage caused by radiation in a subject comprising administering to the subject an effective amount of an agent which is an analog or derivative of benzo[c]chromen-6-one.

2. The method of claim 1 wherein the agent is administered to the subject after the subject has been exposed to radiation.

3. The method of claim 1 wherein the agent is administered to the subject before the subject has been exposed to radiation.

4. The method of claim 1 wherein the agent has the structure of formula I

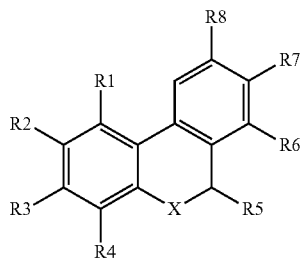

where,
R1=H or alkyl;
R2=H, OH, O-alkyl, amino, O-heterocyc, O-aryl, O-substituted alkyl, where substitution is halo, aryl, or heteroaryl, O-Ac, O—PO3, O—SO3, or OSO2NH2;
R3=H, OH, O-alkyl, O—CH2Aryl, O—CH2heteroaryl, O-alkylaryl, O-acyl, or nitro;
R4=H, Alkyl, CH2Aryl, substituted alkyl, OH, O-alkyl, O-aryl, OCH2Aryl, OCH2Heteroaryl, O-Acyl, OPO3, OSO3, or OSO2NH2;
R5=H, Oxo, aryl, hydroxyl, alkyl, or O-alkyl;
R6=H;
R7=H, Acyl, substituted alkyl, where substitution is hydroxyl or sulfamoyl, alkyl, O-alkyl, or O-substituted alkyl where substitution is O—PO3 or OSO3;
R8=H; and
X=O, N, or S;
in free or pharmaceutically acceptable salt form.

5. The method of claim 1 wherein the agent has the structure of formula II

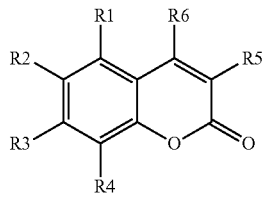

where,
R1=H or alkyl;
R2=H, O-alkyl, OH, amino, O-heterocyc, O-aryl, O-substituted alkyl where substitution is halo, aryl, or heteroaryl, O-Ac, O—PO3, O—SO3, or OSO2NH2;
R3=H, O-alkyl, O-substituted alkyl where substitution is aryl or heteroaryl, OH, O-acyl, or nitro;
R4=H, Alkyl, CH2Aryl, substituted alkyl, O-alkyl, O-aryl, OCH2Aryl, OCH2Heteroaryl, O-Acyl, OPO3, OSO3, or OSO2NH2;
R5=H, Aryl, heteroaryl or substituted alkyl; and
R6=H, Alkyl, or Aryl;
in free or pharmaceutically acceptable salt form.

6. The method of claim 1 wherein the agent has the structure of formula III

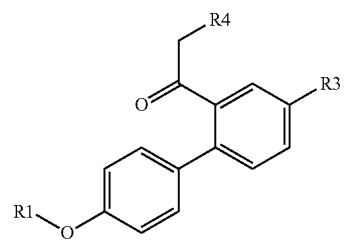

where,
R1=alkyl or H;
R3=Acetyl; and
R4=H or Alkyl;
in free or pharmaceutically acceptable salt form.

7. The method of claim 1 wherein the agent has the structure of formula IV

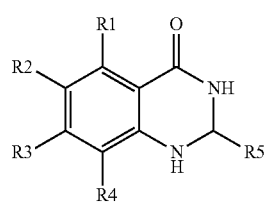

where,
R1=H or F;
R2=H or nitro;
R3=H;
R4=H; and
R5=alkyl, substituted alkyl or aryl;
in free or pharmaceutically acceptable salt form.

8. The method of claim 1 wherein the agent is selected from the group consisting of compounds presented in Table I.

9. The method of claim 8 wherein the agent is SG00529

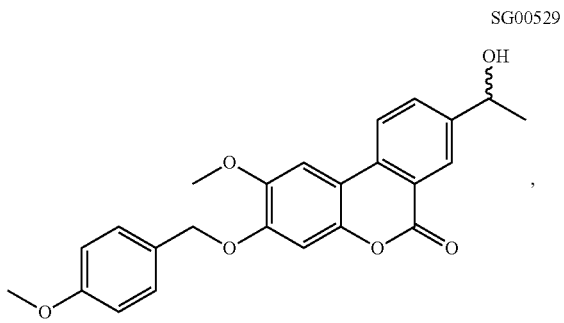 [SMILES: COc1ccc(COc2cc3oc(=O)c4cc(C(C)O)ccc4c3cc2OC)cc1]

SG00529 in free or pharmaceutically acceptable salt form.

10. The method of claim 8 wherein the agent is SG00529.

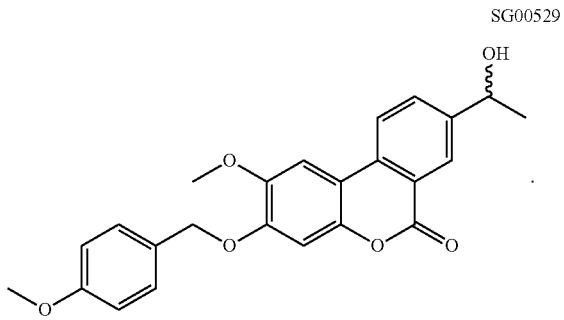 [SMILES: COc1ccc(COc2cc3oc(=O)c4cc(C(C)O)ccc4c3cc2OC)cc1]

SG00529

11. The method of claim 8 wherein the agent is SG00574

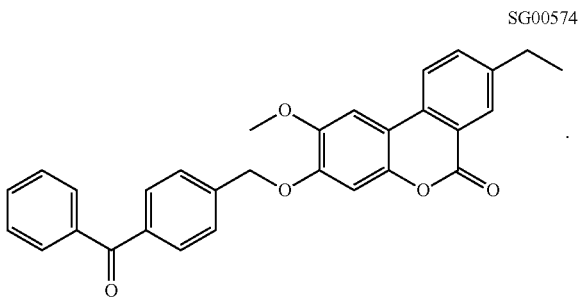 [SMILES: CCc1ccc2c(c1)c(=O)oc1cc(OCc3ccc(C(=O)c4ccccc4)cc3)c(OC)cc12]

SG00574

12. The method of claim 1 wherein the radiation is ionizing radiation.

13. The method of claim 1 wherein the subject is a mammal.

14. The method of claim 1 wherein the subject is human.

15. The method of claim 1 wherein the subject is suffering from or will likely suffer from acute radiation syndrome or radiation sickness.

16. The method of claim 1 wherein the subject is suffering from cancer.

17. The method of claim 16 wherein the subject is being treated with radiation therapy and/or chemotherapy.

18. The method of claim 1 wherein the subject is suffering from leucopenia, neutropenia, purpura, hemorrhage, diarrhea, vomiting, and/or hypotension.

19. The method of claim 1 further comprising administering a cytoprotective agent.

20. A method for reducing radiation damage, reducing potential damage by exposure to radiation, treating damage caused by exposure to radiation, and/or inhibiting formation of damage caused by radiation in a subject comprising administering to the subject an effective amount of an agent which is an analog or derivative of benzo[c]chromen-6-one;
further comprising administering a compound which inhibits the PI3K/Akt/mTOR pathway.

21. The method of claim 1 wherein the agent is administered every hour, 2 hours, 3 hours, 6 hours, or daily following exposure to radiation.

22. The method of claim 1 wherein the agent is administered to achieve a blood plasma level of about 0.1 to about 1000 μM.

23. The method of claim 1 wherein the agent is administered in a dose of about 0.1-1000 mg/kg.

24. The method of claim 1 wherein the agent is administered to the subject within 1 hour, 2 hours, 3 hours, 6 hours, 12 hours, 1 day, or 2 days after the subject has been exposed to radiation.

25. The method of claim 1 wherein the agent is administered to the subject 15 minutes, 30 minutes, 1 hour, 2 hours, 3 hours, 6 hours, 12 hours, 1 day, or 2 days before the subject has been exposed to radiation.

26. A pharmaceutical composition comprising a compound of formula I

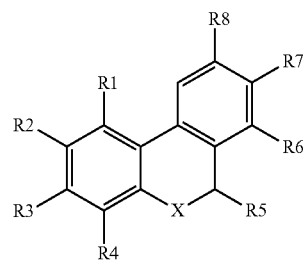

where,
R1=H or alkyl;
R2=H, OH, O-alkyl, amino, O-heterocyc, O-aryl, O-substituted alkyl, where substitution is halo, aryl, or heteroaryl, O-Ac, O—PO3, O—SO3, or OSO2NH2;
R3=H, OH, O-alkyl, O—CH2Aryl, O—CH2heteroaryl, O-alkylaryl, O-acyl, or nitro;
R4=H, Alkyl, CH2Aryl, substituted alkyl, OH, O-alkyl, O-aryl, OCH2Aryl, OCH2Heteroaryl, O-Acyl, OPO3, OSO3, or OSO2NH2;
R5=H, Oxo, aryl, hydroxyl, alkyl, or O-alkyl;
R6=H;
R7=H, Acyl, substituted alkyl, where substitution is hydroxyl or sulfamoyl, alkyl, O-alkyl, or O-substituted alkyl where substitution is O—PO3 or OSO3;
R8=H; and
X=O, N, or S;
in free or pharmaceutically acceptable salt form, in combination with a cytoprotective agent in a pharmaceutically acceptable carrier.

27. A pharmaceutical composition comprising a compound of formula II:

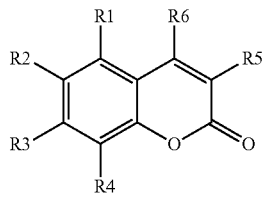

where,
R1=H or alkyl;
R2=H, O-alkyl, OH, amino, O-heterocyc, O-aryl, O-substituted alkyl where substitution is halo, aryl, or heteroaryl, O-Ac, O—PO3, O—SO3, or OSO2NH2;

R3=H, O-alkyl, O-substituted alkyl where substitution is aryl or heteroaryl, OH, O-acyl, or nitro;
R4=H, Alkyl, CH2Aryl, substituted alkyl, O-alkyl, O-aryl, OCH2Aryl, OCH2Heteroaryl, O-Acyl, OPO3, OSO3, or OSO2NH2;
R5=H, Aryl, heteroaryl or substituted alkyl; and
R6=H, Alkyl, or Aryl;
in free or pharmaceutically acceptable salt form, in combination with a cytoprotective agent in a pharmaceutically acceptable carrier.

28. A pharmaceutical composition comprising a compound of formula III

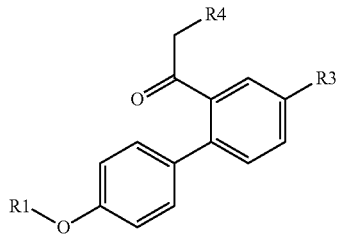

where,
R1=alkyl or H;
R3=Acetyl; and
R4=H or Alkyl;
in free or pharmaceutically acceptable salt form, in combination with a cytoprotective agent in a pharmaceutically acceptable carrier.

29. A pharmaceutical composition comprising a compound of formula IV

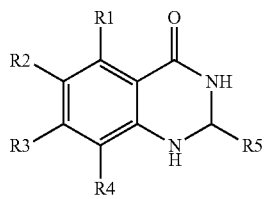

where,
R1=H or F;
R2=H or nitro;
R3=H;
R4=H; and
R5=alkyl, substituted alkyl or aryl;
in free or pharmaceutically acceptable salt form, in combination with a cytoprotective agent in a pharmaceutically acceptable carrier.

* * * * *